US008698083B2

(12) United States Patent
Fuyuki et al.

(10) Patent No.: US 8,698,083 B2
(45) Date of Patent: Apr. 15, 2014

(54) SOLAR CELL EVALUATION METHOD, EVALUATION DEVICE, MAINTENANCE METHOD, MAINTENANCE SYSTEM, AND METHOD OF MANUFACTURING SOLAR CELL MODULE

(75) Inventors: Takashi Fuyuki, Ikoma (JP); Ayumi Tani, Ikoma (JP)

(73) Assignee: National University Corporation Nara Institute of Science and Technology, Nara (JP)

(*) Notice: Subject to any disclaimer, the term of this patent is extended or adjusted under 35 U.S.C. 154(b) by 290 days.

(21) Appl. No.: 13/388,129

(22) PCT Filed: Aug. 3, 2010

(86) PCT No.: PCT/JP2010/063073
§ 371 (c)(1),
(2), (4) Date: Jan. 31, 2012

(87) PCT Pub. No.: WO2011/016441
PCT Pub. Date: Feb. 10, 2011

(65) Prior Publication Data
US 2012/0126120 A1 May 24, 2012

(30) Foreign Application Priority Data

Aug. 4, 2009 (JP) .................................. 2009-181850

(51) Int. Cl.
G01J 5/00 (2006.01)
G01N 21/00 (2006.01)
G01N 21/66 (2006.01)
G01R 31/26 (2014.01)
G01N 21/95 (2006.01)

(52) U.S. Cl.
CPC ............ *G01R 31/2605* (2013.01); *G01N 21/66* (2013.01); *G06T 2207/10048* (2013.01); *G01N 21/9505* (2013.01)
USPC ...................... 250/338.1; 356/237.1; 324/500; 324/501

(58) Field of Classification Search
CPC .. G01R 31/2605; G01R 31/405; G01N 21/66; G01N 21/9505; G06T 2207/10048; H02S 50/00; H04N 5/33
USPC ........ 348/125, 126; 250/214 R, 252.1, 338.1, 250/339.14, 340, 341.4; 356/230, 237.1; 324/501, 500, 511; 438/16, 17; 136/290
See application file for complete search history.

(56) References Cited

U.S. PATENT DOCUMENTS

| 2008/0088829 A1* | 4/2008 | Fuyuki | ........................ 356/230 |
| 2009/0127448 A1* | 5/2009 | Fuyuki | ........................ 250/238 |
| 2010/0266196 A1* | 10/2010 | Kasahara et al. | ............ 382/149 |

FOREIGN PATENT DOCUMENTS

| CN | 101464186 A | 6/2009 |
| JP | 2006-73572 | 3/2006 |

(Continued)

OTHER PUBLICATIONS

International Search Report for PCT/JP2010/063073 mailed Sep. 7, 2010.

(Continued)

*Primary Examiner* — David Porta
*Assistant Examiner* — Yara Green
(74) *Attorney, Agent, or Firm* — Nixon & Vanderhye P.C.

(57) ABSTRACT

A method and device for evaluating a solar cell each of which makes it possible to easily evaluate a defect of a solar cell especially in such a manner that an internal cause defect and an external cause defect are distinguished from each other. The device includes: electric current passing means for passing, in a forward direction, an electric current through a solar cell element constituting the solar cell; light emission detecting means for detecting, out of light emitted from the solar cell element due to the electric current passed by the electric current passing means, light in a first range of wavelengths from 800 nm to 1300 nm and light in a second range of wavelengths from 1400 nm to 1800 nm; and judging means for distinguishing between an internal cause defect and an external cause defect.

22 Claims, 12 Drawing Sheets

(56) References Cited

FOREIGN PATENT DOCUMENTS

| JP | 2009-164165 | 7/2009 |
|---|---|---|
| WO | WO 2006/059615 | 6/2006 |
| WO | WO 2007/129585 | 11/2007 |

OTHER PUBLICATIONS

N. Sakitani et al., "Evaluation of Recombination Velocity at Grain Boundaries in Poly-Si Solar Cells with Laser Beam Induced Current", Solid State Phenomena vol. 93 (2003), pp. 351-354.

J. Isenberg et al., "Spatially Resolved IR-Measurement Techniques for Solar Cells", Presented at the 19$^{th}$ European Photovoltaic Solar Energy Conference, Jun. 7-11, 2004, Paris, pp. 403-407.

E. Rueland et al., "Optical μ-Crack Detection in Combination with Stability Testing for In-Line-Inspection of Wafers and Cells", 20$^{th}$ European Photovoltaic Solar Energy Conference, Jun. 6-10, 2005, Barcelona, Spain, 4 pages.

Japanese Office Action dated Oct. 9, 2013 for Japanese Patent Application No. 201080034247.5 (with translation).

Chinese Office Action dated Oct. 9, 2013 for Chinese Patent Application No. 201080034247.5 (with translation).

* cited by examiner

F I G. 1
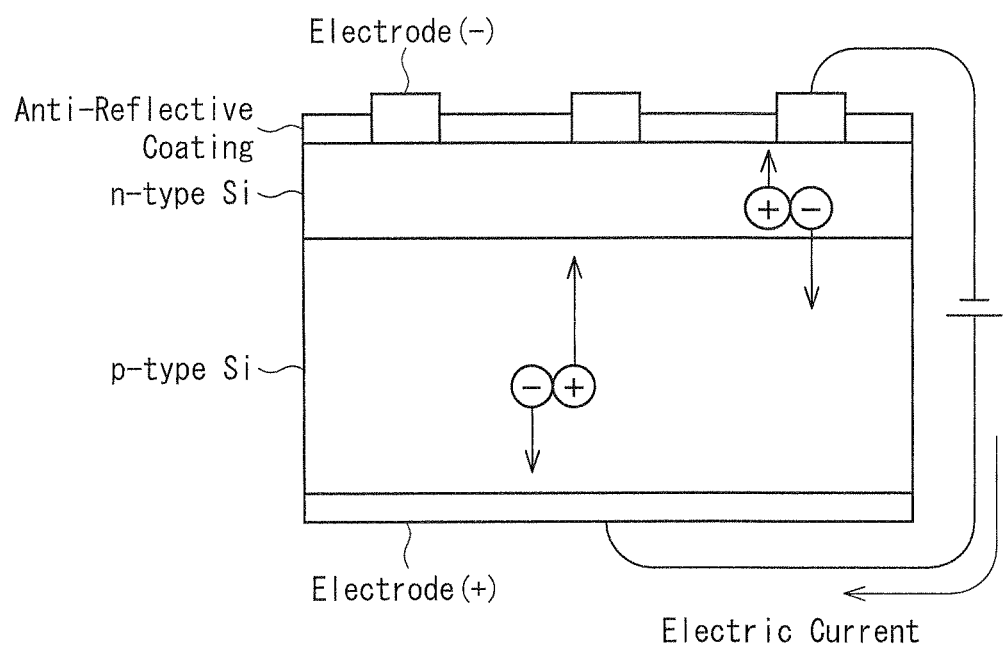

F I G. 3
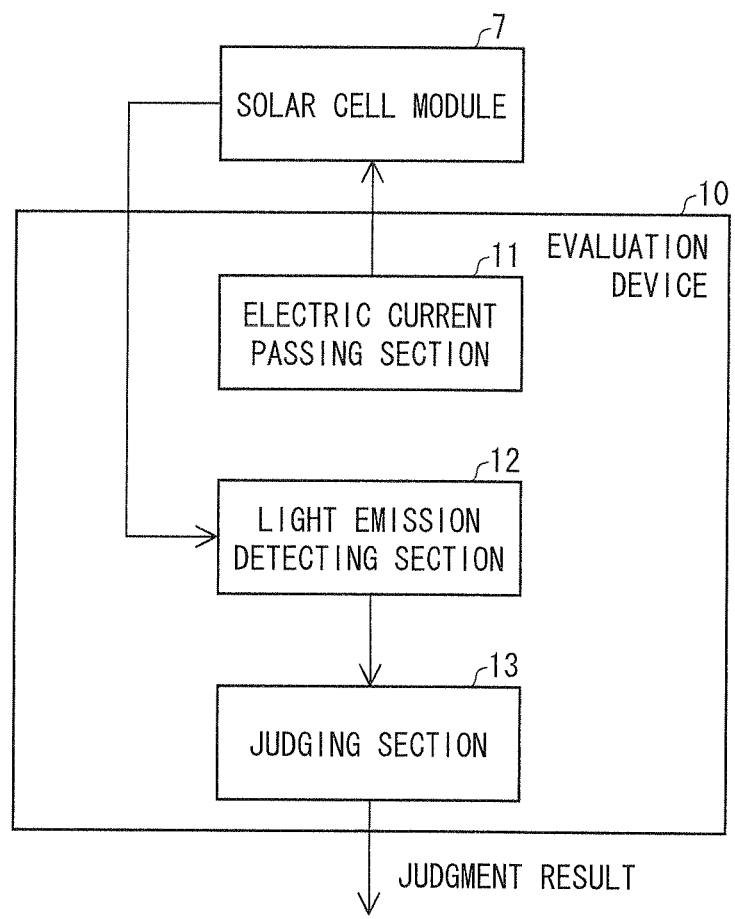

SOLAR CELL EVALUATION METHOD, EVALUATION DEVICE, MAINTENANCE METHOD, MAINTENANCE SYSTEM, AND METHOD OF MANUFACTURING SOLAR CELL MODULE

This application is the U.S. national phase of International Application No. PCT/JP2010/063073 filed 3 Aug. 2010 which designated the U.S. and claims priority to JP 2009-181850 filed 4 Aug. 2009, the entire contents of each of which are hereby incorporated by reference.

TECHNICAL FIELD

The present invention relates to method and device for evaluating a defect of a solar cell easily, and use thereof. Especially, the present invention relates to method and device for evaluating a defect of a solar cell easily by passing an electric current through solar cell elements constituting the solar cell, and analyzing characteristics of light emitted due to the electric current passage, and use thereof.

BACKGROUND ART

For keeping the environment of the earth, use of solar energy is getting popular. Solar cells are implemented on more and more roofs or walls of ordinary buildings and houses. Among the solar cells, development and production of solar cells which incorporate semiconductors that are advantageous to enlarging of size are rapidly progressing as a leading candidate for producing clean energy.

However, in production process of a solar cell, it is difficult to avoid occurrence of defects in the solar cell. This prevents efficient production of solar cells having high performance and high reliability. Further, if defects occur in a solar cell that has been installed during use of the solar cell, performance and reliability of the solar cell decline.

Conventionally, so-called EBIC (Electron Beam Induced Current) and LBIC (Laser Beam Induced Current), that is, methods for measuring a current or voltage induced by using an electron beam or laser beam and thereby analyzing diffusion length of minority carriers and defects (grain boundary/transgranular), are widely used as the method for detecting/evaluating the defects of the solar cell, for example. By the EBIC or LBIC, it is possible to measure a degree of an elective activity or diffusion length of the minority carriers in solar cells locally and to evaluate conversion efficiency and quality of the solar cell (see Non Patent Literature 1). Moreover, an apparatus has been revealed, which apparatus analyzes, based on infrared light intensity, distribution of heat generated due to a bias in a forward direction, so as to detect a short circuit section (see Non Patent Literature 2). Furthermore, a technique has also been revealed that a back side of a substrate is exposed to strong light so as to detect leakage of light, which as a result detects a substrate crack (see Non Patent Literature 3).

The inventors of the present invention found that, in a case where an electric current is passed through a solar cell in a forward direction, luminescence is observed even under normal carrier introducing condition at room temperature, and developed a technique for examining a defect of a solar cell by analyzing an image of the luminescence (see Patent Literature 1).

By the way, defects in solar cells are generally largely classified into defects caused by internal factors (internal cause defects) and defects caused by external factors (external cause defects). The internal cause defects are defects such as crystal defect, dislocation, grain boundaries and the like that are caused by physical properties of a solar cell. The internal cause defects affect functions of a solar cell, but do not affect reliability of materials constituting the solar cell very much. Meanwhile, the external cause defects are mechanical defects of solar cells such as a substrate crack (e.g., microcrack), electrode rupture, loose connection and the like. The external cause defects cause adverse effect on reliability of solar cells and production yield of solar cells, and therefore become deciding factors in efficient mass production of highly reliable solar cells.

As described above, internal cause defects cause a decline in performance of a solar cell, and causes a deterioration in power generation efficiency of the solar cell if left untreated, but an influence of the internal cause defects is small in terms of long-term reliability. Meanwhile, if external cause defects are left untreated, reliability gradually declines, and in the worst case, a solar cell is broken. Accordingly, external cause defects cause a greater adverse effect than internal cause defects. In order to properly cope with a defect that has occurred in a solar cell during production or use of the solar cell, it is therefore important to clarify whether the defect is an internal cause defect or an external cause defect. However, in the conventional arts, it is impossible to distinguish between an internal cause defect and an external cause defect.

In view of this, the inventors of the present invention improved the technique of Patent Literature 1 and developed a technique in which a direct current is passed through a solar cell in a forward direction and the solar cell is heated, and an internal cause defect and an external cause defect are distinguished from each other by using, as an indicator, light emission characteristics based on a change of a heating temperature (Patent Literature 2). According to this technique, an internal cause defect, which depends on a change of temperature, becomes unclear as the temperature rises, whereas an external cause defect, which does not depend on a change of temperature, appears prominently in a high temperature region. It is thus possible to distinguish between an internal cause defect and an external cause defect.

CITATION LIST

Patent Literature 1
WO 2006/059615 (Publication Date: Jun. 8, 2006)
Patent Literature 2
WO 2007/129585 (Publication Date: Nov. 15, 2007)
Non-Patent Literature 1
N. Sakitani, et al., "Evaluation of Recombination Velocity at Grain Boundaries in Poly-Si Solar Cells with Laser Beam Induced Current" Solid State Phenomena Vol. 93 (2003), pp. 351-354
Non-Patent Literature 2
J. Isenberg, et al., "SPATIALLY RESOLVED IR-MEASUREMENT TECHNIQUES FOR SOLAR CELLS" Presented at the 19th European Photovoltaic Solar Energy Conference, 7-11 Jun. 2004, Paris
Non-Patent Literature 3
E. Rueland, et al., "OPTICAL p-CRACK DETECTION IN COMBINATION WITH STABILITY TESTING FOR IN-LINE-INSPECTION OF WAFERS AND CELLS" 20th European Photovoltaic Solar Energy Conference, 6-10 Jun. 2005, Barcelona, Spain

SUMMARY OF INVENTION

Technical Problem

As described above, according to the technique disclosed in Patent Literature 2, it is possible to distinguish between an internal cause defect and an external cause defect. However, as a result of expansion of the market scale of solar cells and rapid increase in production amount of solar cells, a new solar cell evaluation technique is required.

The present invention was attained in view of the above problems, and an object of the present invention is to provide solar cell evaluation method and device for evaluating a defect of a solar cell easily especially in a manner such that an internal cause defect and an external cause defect are distinguished from each other, and use thereof.

Solution to Problem

The inventors of the present invention found that in a case where an electric current is passed through a solar cell in a forward direction, an internal cause defect portion and an external cause defect portion of the solar cell are different in characteristics of light emitted due to electroluminescence. Based on this new finding, the inventors of the present invention accomplished the present invention. The present invention encompasses the following inventions.

A method of the present invention for evaluating a solar cell is a method for evaluating a defect of a solar cell, which includes the steps of: (a) passing, in a forward direction, an electric current through a solar cell element constituting the solar cell; (b) detecting, out of light emitted from the solar cell element due to the electric current passed in the step (a), light in a first range of wavelengths from 800 nm to 1300 nm and light in a second range of wavelengths from 1400 nm to 1800 nm; and (c) distinguishing between an internal cause defect and an external cause defect by using, as indicators, a light emission intensity of the light in the first range and a light emission intensity of the light in the second range out of the light detected in the step (b).

A device of the present invention for evaluating a solar cell is a device for evaluating a defect of a solar cell, which includes: electric current passing means for passing, in a forward direction, an electric current through a solar cell element constituting the solar cell; light emission detecting means for detecting, out of light emitted from the solar cell element due to the electric current passed by the electric current passing means, light in a first range of wavelengths from 800 nm to 1300 nm and light in a second range of wavelengths from 1400 nm to 1800 nm; and judging means for distinguishing between an internal cause defect and an external cause defect by using, as indicators, a light emission intensity of the light in the first range and a light emission intensity of the light in the second range out of the light detected by the light emission detecting means.

Advantageous Effects of Invention

The method and device of the present invention for evaluating a solar cell produces an effect that it is possible to easily distinguish among defects of the solar cell, especially between an internal cause defect caused due to physical properties of the solar cell and an external cause defect which is a mechanical defect. This makes it possible to evaluate type and/or quantity of defects of the solar cell. Further, since the present invention utilizes electroluminescence, a large facility is not necessary. It is therefore possible to evaluate the solar cell as a product (as a product completed in the manufacturing factory or as a product implemented on a construction).

Further, the solar cell maintenance method and maintenance system of present invention do not require a large-sized device, and make it possible to evaluate quality of a solar cell easily. It is therefore possible to regularly perform maintenance of even a solar cell implemented on a construction. Consequently, quality of a solar cell module can be kept at a certain level.

Further, according to the method of the present invention for producing a solar cell module, it is possible to detect defects while distinguishing between an internal cause defect and an external cause defect. Accordingly, it is possible to repair or replace only a serious defective part. This produces an effect that a solar cell module can be produced efficiently.

BRIEF DESCRIPTION OF DRAWINGS

FIG. 1 is a diagram schematically illustrating how an electric current is passed, in a forward direction, through a solar cell element.

FIG. 3 is a functional block diagram schematically illustrating an example of the device of the present embodiment for evaluating a solar cell.

Figure 11:
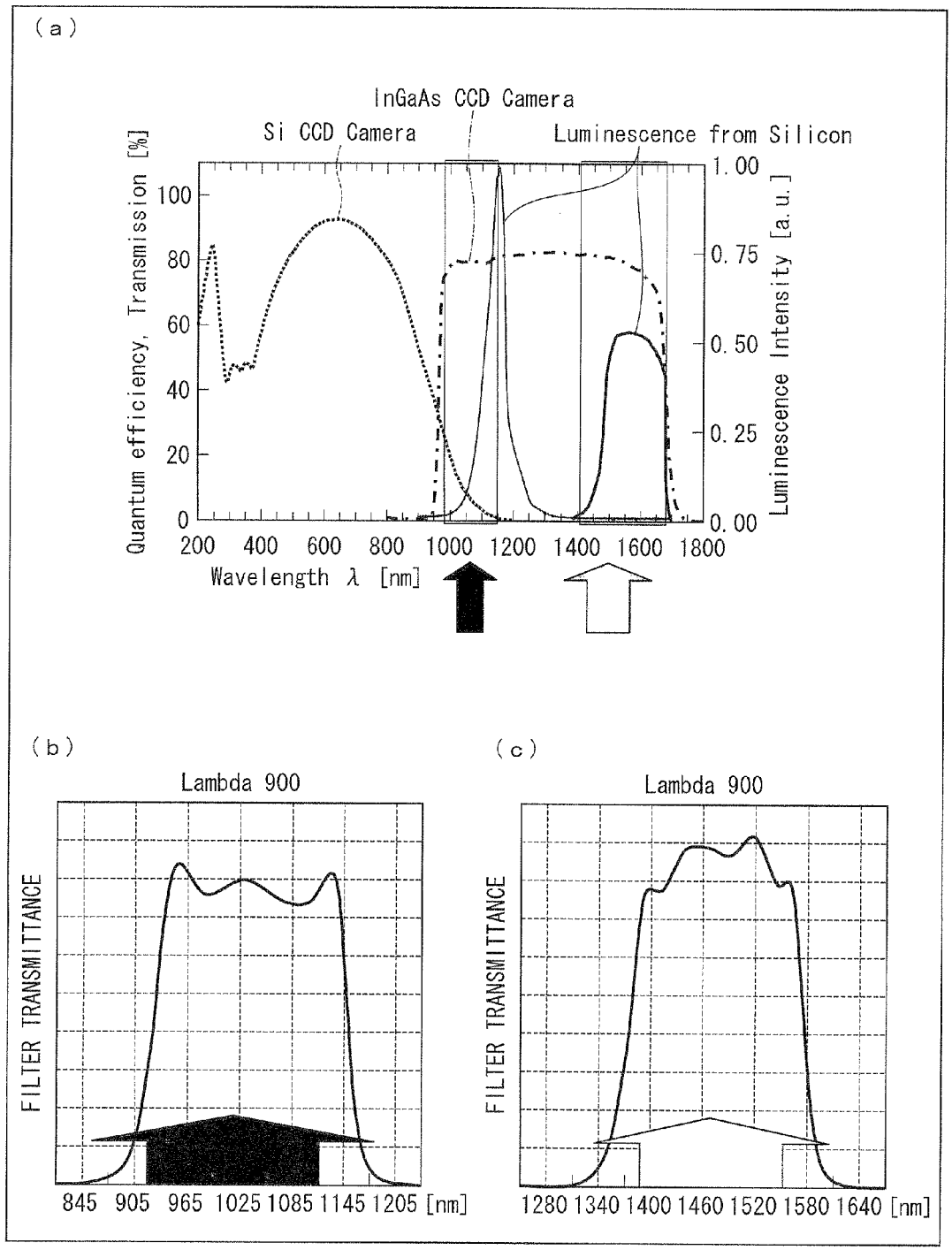

(a) of FIG. 11 is a diagram illustrating relationship between a light emission intensity (luminescence intensity) and a wavelength of light generated by passing an electric current through a solar cell module, and (b) and (c) of FIG. 11 are diagrams illustrating characteristics of a band-pass filter for a wavelength of 1100 nm and a band-pass filter for a wavelength of 1500 nm, respectively.

Figure 12:
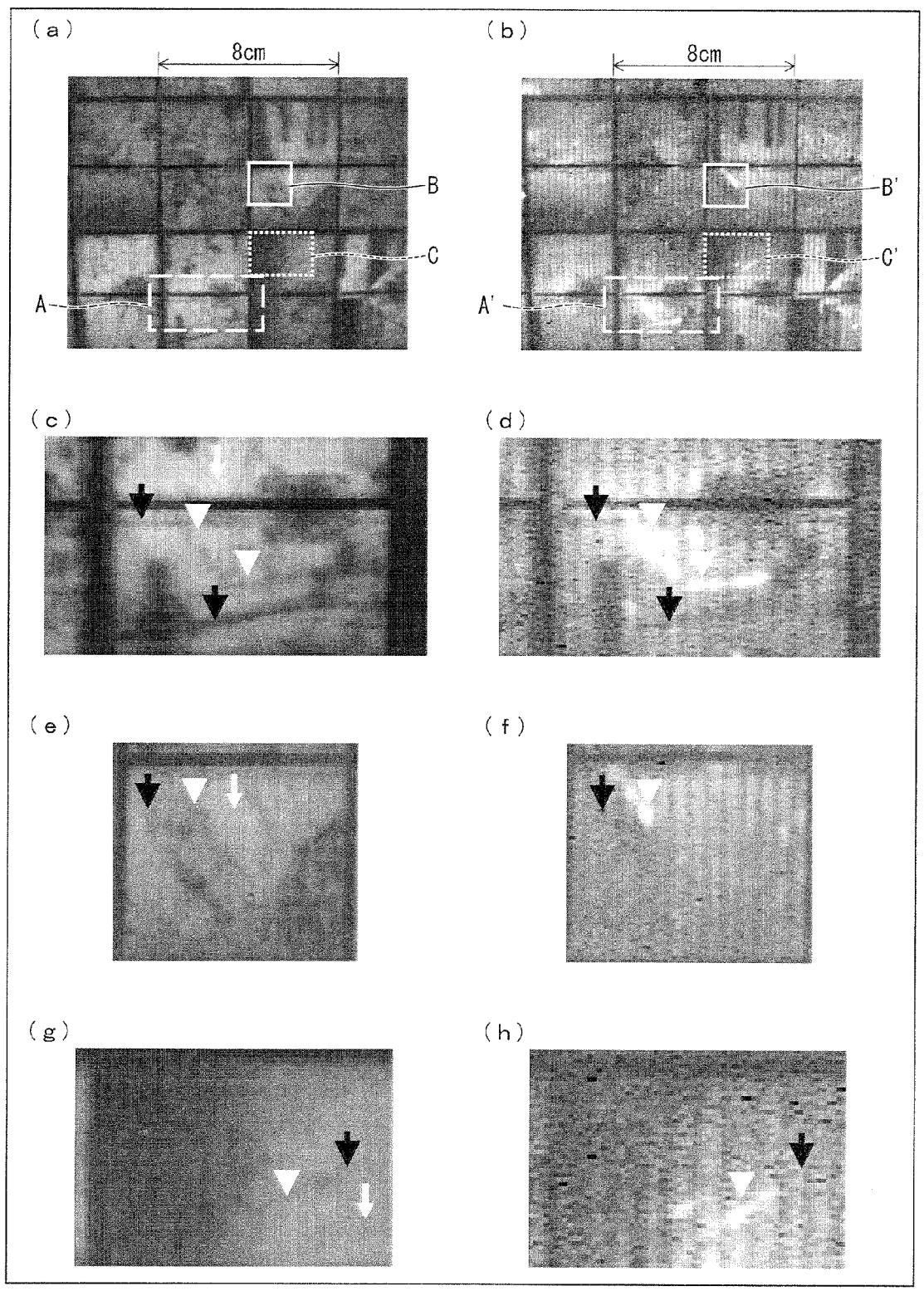

FIG. 12 is a diagram showing an image obtained by picturing emission of light emitted from a solar cell module, (a) and (b) of FIG. 12 are diagrams showing an image obtained by picturing emission of light of 1100 nm emitted from the solar cell module and an image obtained by picturing emission of light of 1500 nm emitted from the solar cell module, (c), (e), and (g) of FIG. 12 are enlarged views of A, B, and C shown in (a) of FIG. 12, and (d), (f), and (h) of FIG. 12 are enlarged views of A', B', and C' shown in (b) of FIG. 12

DESCRIPTION OF EMBODIMENTS

The inventors of the present invention have conducted researches on evaluation of solar cell performance. In particular, the inventors of the present invention uniquely focused attention on relation between electroluminescence and solar cell performance, and have developed revolutionary solar cell evaluation techniques (Patent Literatures 1 and 2). This time, the inventors of the present invention found that in a case where a direct current is applied to solar cell elements, light is emitted due to electroluminescence in two different wavelength ranges, i.e., the vicinity of a wavelength of 1100 nm and the vicinity of a wavelength of 1500 nm. In an electroluminescence phenomenon which occurs in a case where an electric current is passed through a solar cell, a light emission intensity of light of a shorter wavelength (the vicinity of 1100 nm) is stronger than that of light of a longer wavelength (the vicinity of 1500 nm).

The inventors of the present invention studied meaning of the two types of light having the different wavelengths. Conventionally, there are reports on photoluminescence regarding light emission from a deep level of silicon crystal (for example, Michio TAJIMA and Yoshiaki MATSUSHITA JAPANESE JOURNAL OF APPLIED PHYSICS VOL. 22, NO. 9, SEPTEMBER, pp. L589-L591 (1983))). This document reports that light emission related to transition of monocrystal Si occurs in the vicinity of 0.8 eV to 0.9 eV.

The inventors of the present invention uniquely reasoned that light emission due to electroluminescence in the vicinity of the wavelength of 1500 nm found this time is associated with the photoluminescence light emission phenomenon, and made further consideration. As a result, the inventors of the present invention concluded, by matching a change of light emission on a two-dimensional image with a distribution of defects, that light emission in the vicinity of the wavelength of 1100 nm in electroluminescence is light caused by interband transition of a solar cell, whereas light in the vicinity of the wavelength of 1500 nm is light caused by an internal cause defect (especially transition of a crystalline state, composite with impurities, etc.) of a solar cell element.

The inventors of the present invention applied this revolutionary new finding to defect discrimination using two-dimensional imaging, and thus completed the present invention. The discovery of the phenomenon, estimation and examination of the mechanism, and application of the finding could be accomplished only by the inventors of the present invention, and could not have been attained by a general skilled in the art. Note that the background to the completion of the present invention is described just to help the understanding of the present invention, and must not be interpreted as description limiting the present invention.

The following describes an embodiment of the present invention in detail.

[1. Method for Evaluating Solar Cell]

A method of the present invention for evaluating a solar cell is a method for evaluating a defect of the solar cell which includes the steps of: (a) passing an electric current, in a forward direction, through a solar cell element constituting the solar cell; (b) detecting, out of light emitted from the solar cell element due to the step (a), light in a first range of wavelengths from 800 nm through 1300 nm and light in a second range of wavelengths from 1400 nm through 1800 nm; and (c) distinguishing between an internal cause defect and an external cause defect by using, as indicators, light emission intensity of the light in the first range and light emission intensity of the light in the second range detected in the step (b).

The expression "evaluate a defect of a solar cell" used herein encompasses detection of a defect in a solar cell (which hereinafter encompasses, for example, a solar cell module, a solar cell panel, or a solar cell element itself), judgment as to whether or not a defect is present in a solar cell, and evaluation of quantity and/or type of defects of a solar cell.

The expression "evaluate a quantity of defects of a solar cell" encompasses calculation of an absolute number of defects of a solar cell and judgment as to whether a quantity of defects of a solar cell is smaller or larger than a predetermined quantity.

The expression "evaluate a type of a defect of a solar cell" means identification of a type of a defect of a solar cell, and specifically, encompasses distinguishment between an internal cause defect and an external cause defect.

The term "solar cell element" is a minimum unit of element which generates an electric current in response to light due to a photoconductive effect and/or a photovoltaic effect, and has, for example, a size of 10 cm×10 cm through 15 cm×15 cm. The term "solar cell module" refers to a module obtained by linking a plurality of solar cell elements, and is obtained, for example, by linking 10 to 50 solar cell elements and has, for example, a size of approximately 0.5 m×0.5 m through 1.0 m×1.0 m. The term "solar cell module" used herein encompasses "solar cell panel" which is obtained by combining the modules. Furthermore, the term "solar cell" is to mean any one or all of the solar cell element, solar cell module, and solar cell panel.

The following describes the steps of the method of the present invention in detail. Note that specific steps other than these step, materials, conditions, apparatuses and devices to be used, etc. are not limited in particular, and conventionally known methods etc. can be suitably used.

[1-1. Electric Current Passing Step]

The electric current passing step is not limited in particular, provided that it is a step of passing, in a forward direction, an electric current through a solar cell element constituting a solar cell. The electric current passed through the solar cell element may be a direct current or a pulse current. The following description deals with a case where a direct current is passed through a solar cell element.

Figure 2:
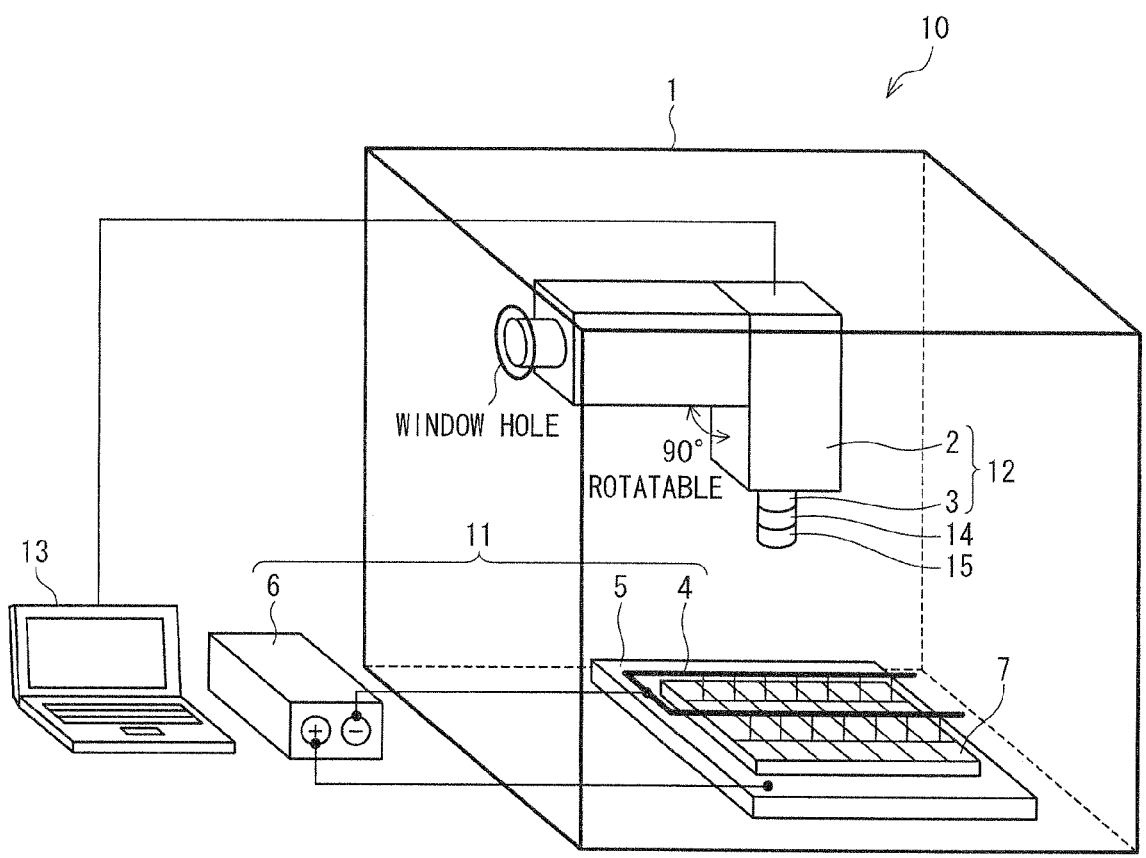
FIG. 2 is a diagram schematically illustrating an example of a device of the present embodiment for evaluating a solar cell.

In the electric current passing step, the wording "passing the direct current in the forward direction" means to bias in the so-called forward direction, as illustrated in FIG. 2. The direct current is passed therethrough in the forward direction by externally applying a voltage which is positive (+) on the p-type region side and negative (−) on the negative region side of the pn junction. This causes the solar cell element to emit light due to electroluminescence.

In this step, a device for passing the electric current through the solar cell element may be a power supply or the like conventionally known, and is not particularly limited. For example, a general constant current source may be used as the device for passing the electric current through the solar cell element. A device for passing a direct current through the solar cell element may be a conventionally known direct current power supply.

[1-2. Light Emission Detecting Step]

The light emission detecting step is not limited in particular in terms of its specific method etc., provided that it is a step of detecting, out of light emitted from the solar cell element due to the electric current passing step, light in a first range of wavelengths from 800 nm through 1300 nm and light in a second range of wavelengths from 1400 nm through 1800 nm. A conventionally known technique can be suitable used for the light emission detecting step.

In this step, light detecting means conventionally known may be employed, which is capable of detecting light emitted from the solar cell element (light having a wavelength in the vicinity of 800 nm through 1800 nm). A light detecting means to be employed in the light emission detecting step is not particularly limited in terms of specific configuration etc.

The light detecting means may be, for example, a light detecting device such as a CCD camera or an image intensifier. Examples of the CCD camera include an InGaAs CCD camera (XEVA-1.7 series produced by Xenics or C8250-20 produced by Hamamatsu Photonics K.K.), a Si CCD camera (C9299-02 produced by Hamamatsu Photonics K.K.), and the like. The Si CCD camera is capable of detecting light of a wavelength range from 200 nm to 1200 nm. Meanwhile, the InGaAs CCD camera is capable of collectively detecting light of a wavelengths range from 800 nm to 1800 nm, and is preferably used.

Examples of the image intensifier include an image intensifier (product number: V8071U-76) produced by Hamamatsu Photonics K.K. that is capable of detecting light of wavelengths in a range from 360 nm to 1100 nm.

By using such a light detecting device such as a CCD camera or an image intensifier, light emission in a solar cell can be observed in the form of an image. That is, a two-dimensional in-plane distribution of light emission in the solar cell can be collectively measured, and therefore a defect of the solar cell can be easily and speedily evaluated.

In this step, it is preferable that the light in the first range and the light in the second range are detected by use of single light detecting means. This eliminates the need for replacement of the light detecting means and position adjustment accompanying the replacement, thereby making it possible to more easily carry out this step. In this case, an InGaAs CCD can be for example used. Note that the light in the first range and the light in the second range may be detected by using different light detecting means, respectively. In this case, for example, a Si CCD camera and an InGaAs CCD camera may be used together or an image intensifier (V8071U-76 produced by Hamamatsu Photonics K.K.) and an InGaAs CCD camera can be used together. Further, these three types of light detecting devices can be used in combination.

In a case where light of wavelengths in a range from 800 nm to 1800 nm, i.e., light in the first range and the light in the second range are concurrently detected by use of a single light detecting means such as an InGaAs CCD camera as described above, it is preferable that band pass filters which selectively transmit the respective light be used. This makes it possible to efficiently detect the light in the first range and the light in the second range separately. That is, in this step, it is preferable that the light is detected by use of (i) light detecting means that is capable of concurrently detecting the light in the first range and the light in the second range, (ii) a band pass filter which selectively transmits the light in the first range, and (iii) a band pass filter which selectively transmits the light in the second range.

Each of the band-pass filters can be disposed in any position between the solar cell and the detecting means so that light emitted from the solar cell element passes through the band-pass filter before reaching the light detecting means. For example, each of the band-pass filters may be provided in a lens part of the light detecting means. Examples of the band-pass filter which selectively transmits the light in the first range include BROAD BANDPASS FILTER (BBP-0910-1170C produced by SPECTROGON), and examples of the band-pass filter which selectively transmits the light in the second range include BROAD BANDPASS FILTER (BBP-1350-1600C produced by SPECTROGON).

As described above, since a wavelength range and a light emission intensity of light emitted from the solar cell element vary depending on a type of a defect, the light of the respective wavelengths is detected by use of different band-pass filters that transmits different ranges of wavelengths. By comparing light emission intensities of the light, it is possible to easily and speedily evaluate a defect.

As described later in Examples, detection sensitivity to the light in the first range is higher than detection sensitivity to the light in the second range. Accordingly, in a case where an image of the light in the first range is acquired, a period of time required for electric current application and a period of time required for taking the image can be made shorter as compared with a case where an image of the light in the second range is acquired. In the solar cell evaluation method of the present invention, it is therefore preferable that $j1<j2$ and/or $t1<t2$ are satisfied where j1 is an amount of the electric current passed through the solar cell element in the electric current passing step in order to detect the light in the first range, t1 is a period of time for detection of the light in the first range in the light emission detecting step, j2 is an amount of the electric current passed through the solar cell element in the electric current passing step in order to detect the light in the second range, and t2 is a period of time for detection of the light in the second range in the light emission detecting step.

[1-3. Judging Step]

The judging step is not limited in particular, provided that it is a step of distinguishing between an internal cause defect and an external cause defect by using, as indicators, the light emission intensity of the light in the first range detected in the light emission detecting step and the light emission intensity of the light in the second range detected in the light emission detecting step.

In the judging step, a process is carried out in which the light emission intensity of the light in the first range and the light emission intensity of the light in the second range are compared with a first threshold value and a second threshold value, respectively, and results thus obtained are considered, for example. A method for the comparison is not limited in particular, and can be, for example, a conventionally known method in which (i) an image of the light in the first range and an image of the light in the second range are acquired, (ii) the light emission intensity of the light in the first range in the image of the light in the first range is compared with a first threshold value, (iii) the light emission intensity of the light in the second range in the image of the light in the second range is compared with a second threshold value, and (iv) results thus obtained are considered. Another method for the comparison may be a method in which comparison with a controlling image that is prepared in advance is carried out. In these cases, the image of the light in the first range and the image of the light in the second range may be compared with respective threshold values separately or may be compared with respective threshold values in a state in which these images are superimposed on each other.

It is of course possible that instead of using the images, the light emission intensities of the two types of light are turned into numerical values, the numerical values thus obtained are concurrently compared with the first and second threshold values, respectively, and results thus obtained are considered. The light emission intensities may be turned into numerical values, for example, by digitalizing the light emission intensities of the light detected by the light detecting means. For example, in the light emission detecting step, the light emission intensities of the light emitted from the solar cell element can be digitized with the use of the light detecting means such as a CCD camera or an image intensifier. In a case where the light emission intensities are turned into numerical values as above, the judging step can be precisely carried out.

That is, in the judging step, for example, (i) in a case where the light emission intensity in the first range is not more than a first threshold value, it is determined that a defect is present, (ii) in a case where the light emission intensity of the light in the second range is not less than the second threshold value in a portion judged, in the step (i), as a portion having the defect, it is determined that there is an internal cause defect in the portion, whereas in a case where the light emission intensity of the light in the second range is smaller than the second threshold value in the portion judged, in the step (i), as a portion having the defect, it is determined that an external cause defect is present in the portion. According to this arrangement, first, a portion in which a defect is present is detected on the basis of the light emission intensity of the light in the first range, and then it can be determined, on the basis of the light emission intensity of the light in the second range, whether the defect thus detected is an internal cause defect or an external cause defect.

Such sequential defect judging steps can be, for example, carried out when evaluation of a defect is performed for each portion of the solar cell element based on all data of the light emission intensity of the light in the first range and the light emission intensity of the light in the second range which are processed by a computer or the like after being acquired.

It is also possible that, in the judging step, (iii) a portion in which the light emission intensity of the light in the first range is not more than a first threshold value and the light emission intensity of the light in the second range is not less than a second threshold value is judged as an internal cause defect, and (iv) a portion in which the light emission intensity of the light in the first range is not more than the first threshold value and the light emission intensity of the light in the second range is smaller than the second threshold value is judged as an external cause defect. The order in which the step (iii) and the step (iv) are carried out is not limited in particular. The step (iv) may be carried out after the step (iii) or vice versa. Alternatively, the step (iii) and the step (iv) may be carried out concurrently. In a case where the step (iii) and the step (iv) are carried out concurrently, a defect of a solar cell can be evaluated more speedily as compared with a case where the step (i) and the step (ii) are carried out.

The "first threshold values" used in the step (i) through (iv) may be different from each other or identical to each other, and the "second threshold values" used in the step (i) through (iv) may be different from each other or identical to each other. For example, there may be a case where the "first threshold value" used in the step (i) is identical to the "first threshold value" used in the steps (iii) and (iv) that is to be compared with the light emission intensity of the light in the first range and the "second threshold value" used in the step (ii) is identical to the "second threshold value" used in the steps (iii) and (iv) that is to be compared with the light emission intensity of the light in the second range.

The "first threshold value" and the "second threshold value" can be regarded as values for judging a defect, and can be appropriately set by a user in consideration of desired performance of the solar cell element, yield, etc. In a case where the first threshold value is set low, yield can be improved, whereas in a case where the first threshold value is set high, a solar cell element of higher quality can be obtained. In a case where the second threshold value is set high, yield can be improved, whereas the second threshold value is set low, a solar cell element of higher quality can be obtained. For example, the threshold values may be set by (i) specifying, in advance by use of a conventionally known method, portions of the solar cell element in which portions an internal cause defect and/or an external cause defect is present, and (ii) turning, into numerical values, light emission intensity of light in the first range emitted from these portions and light emission intensity of light in the second range emitted from these portions. Such threshold values are so-called controlling values. Such threshold values may be set based on a solar cell to be evaluated or may be set in advance based on another solar cell.

For example, the "first threshold value" may be a value of a light emission intensity of light in the first range emitted from a normal portion of a solar cell element by passing an electric current through the solar cell element in the electric current passing step or may be 90%, 80%, 70%, 60%, 50%, 40%, 30%, 20%, or 10% of the light emission intensity of light in the first range emitted from the normal portion of the solar cell element. In a case where the first threshold value is set to a value close to the light emission intensity of light emitted from the normal portion of the solar cell element, even a minor defect can be detected. Meanwhile, a more severe defect can be detected as the first threshold value is made smaller as compared with the light emission intensity of light emitted from the normal portion of the solar cell element. Note that the term "normal portion" refers to a portion of a solar cell in which portion neither an internal cause defect nor an external cause defect is present. Note that it is preferable that a threshold value be measured and set in advance.

Similarly, the "second threshold value" may be a light emission intensity of light in the second range emitted from an internal cause defect portion of a solar cell element by passing an electric current through the solar cell element in the electric current passing step or may be a value slightly smaller than the light emission intensity of light in the second range emitted from the internal cause defect portion of the solar cell element, for example, approximately 90%, 80%, 70%, 60%, or 50% of the light emission intensity of light in the second range emitted from the internal cause defect portion of the solar cell element.

The term "light emission intensity" refers to an intensity of light of a predetermined wavelength range, and can be, for example, a peak value or an integration value of a light emission spectrum in a predetermined range. A light emission intensity of light in the first range and a light emission intensity of light in the second range can be obtained by creating a light emission spectrum of light emitted from a solar cell and obtaining peak values or integration values of the light emission spectrum in the first range and the second range, by using a conventionally known method.

As described above, the judging step is not limited in particular, provided that it is a step of making a judgment by comparing a measured light emission intensity with a reference value. A conventionally known method can be suitably used as a specific method for the judging step.

The above description dealt with a case where a defect of a solar cell is evaluated quantitatively by turning a light emission intensity into a value, but it is needless to say that a defect of a solar cell can be evaluated qualitatively only by checking whether the light emission intensity of the light is strong or weak, for example. Also in this case, the above method can be appropriately employed.

[1-4. Image Generating Step]

The method of the present invention for evaluating a solar cell may further include an image generating step. The image generating step is not limited in particular, provided that it is a step of generating a first image based on a light emission intensity of light in the first range detected in the light emission detecting step and a second image based on a light emission intensity of light in the second range detected in the light emission detecting step. In this step, a light detecting device, such as a CCD camera or an image intensifier, which is capable of acquiring an image of light emission from a solar cell can be used as described above. With the use of such a light detecting device, a light emission intensity of detected light can be digitized and thus can be turned into a numerical value. The light detecting device can be used not only for detection of light emission from a solar cell element in the light emission detecting step, but also for generation of an image of the detected light emission in the image generating step.

The expression "image based on a light emission intensity" refers to an image indicative of a distribution of a light emission intensity of light in a solar cell element, and can be, for example, a two-dimensional in-plane distribution of a light emission intensity in a solar cell element. With the use of such an image, it is possible to know from which portion of a solar cell element the light is emitted and how strong a light emission intensity of the light is.

The image generating step should at least include generating the image in the from of data, but may further include displaying the image thus generated on a display section such as a display. In a case where the image is displayed on a display, the judging process (later described) can be carried out visually.

In a case where the method of the present invention for evaluating a solar cell includes the image generating step, the judging step is not limited in particular, provided that it is a step of distinguishing between an internal cause defect and an external cause defect by using, as indicators, a light emission intensity of light in the first range in a first image generated in the image generating step and a light emission intensity of light in the second range in a second image generated in the image generating step.

In such a judging step, for example, a process is carried out in which a light emission intensity of light in the first range in a first image and a light emission intensity of light in the second range in a second image are compared with a first threshold value and a second threshold value, respectively, and results thus obtained are considered. A method for the comparison is not limited in particular, and can be, for example, a method in which (i) a light emission intensity of light in the first range in a first image is compared with the first threshold value, (ii) a light emission intensity of light in the second range in a second image is compared with the second threshold value, and (iii) results thus obtained are considered. Alternatively, the method for the comparison may be a method in which comparison with a controlling image that is prepared in advance is carried out. As for the other matters concerning this judging step, the description in [1-3] can be referred to, and therefore the explanation of the other matters is omitted.

[1-5. Evaluation Under Actual Operating Conditions]

The identification of defects of a solar cell element based on spectroscopic analysis of light emitted due to electroluminescence is applicable to all types of solar cell elements. Specifically, the method of the present invention for evaluating a solar cell is applicable to any solar cell elements such as a crystalline or noncrystalline solar cell element, a compound-semiconductor solar cell element, a dye-sensitized solar cell element, or an organic solar cell element. For example, a solar cell element to be evaluated by the method of the present invention for evaluating a solar cell is not limited in particular, provided that it is a solar cell element which contains, as a main component, a conventionally known semiconductor material. However, it is preferable that a solar cell element to be evaluated by the method of the present invention for evaluating a solar cell includes, as a main constituent member, a silicon semiconductor. The silicon semiconductor used in the solar cell element is preferably a monocrystalline, polycrystalline, or amorphous silicon semiconductor. The expression "include as a main constituent member" used herein means that any other members and components can be provided in the solar cell element as long as the solar cell element includes, as a main constituent member, a silicon semiconductor.

Above all, the solar cell element to be evaluated by the method of the present invention for evaluating a solar cell is preferably a solar cell element which includes, as a main constituent member, a polycrystalline silicon semiconductor. In a case where the solar cell element is produced by using, as a main constituent member, a polycrystalline silicon semiconductor, it is difficult to obtain a uniform in-plane distribution. Accordingly, quality evaluation and performance checking using the evaluation method of the present invention are very important.

As described later in Examples, in a case where an electric current is passed, in a forward direction, through a solar cell element which includes, as a main constituent member, a monocrystalline and/or polycrystalline silicon semiconductor, light in the first range of wavelengths from 800 nm to 1300 nm, preferably from 900 nm to 1250 nm, more preferably from 1100 nm to 1200 nm and light in the second range of wavelengths from 1400 nm to 1800 nm, preferably from 1500 nm to 1700 nm, more preferably from 1550 nm to 1650 nm are strongly emitted. A peak of the light in the first range is a wavelength of 1150 nm, and a peak of the light in the second range is a wavelength of 1600 nm.

It is preferable that a density of an electric current passed in the electric current passing step is substantially same as a density of an operating electric current of the solar cell element. The expression "operating electric current of the solar cell element" means an electric current actually generated by photoelectric conversion when the solar cell element to be evaluated is irradiated by sun light.

Specifically, in order to generate light in the first range which has a larger light emission intensity, it is only necessary that a density of an electric current to be passed is 5 mA/cm$^2$ to 1000 mA/cm$^2$, specifically 50 mA/cm$^2$ to 800 mA/cm$^2$, more specifically 100 mA/cm$^2$ to 500 mA/cm$^2$, although the density of an electric current to be passed is not limited in particular. In order to generate light in the second range which has a larger light emission intensity, it is only necessary that a density of an electric current to be passed is 10 mA/cm$^2$ to 3000 mA/cm$^2$, specifically 100 mA/cm$^2$ to 2000 mA/cm$^2$, more specifically 500 mA/cm$^2$ to 1500 mA/cm$^2$, although the density of an electric current to be passed is not limited in particular. Needless to say, a density of an electric current to be passed is not limited to these values, and can be varied appropriately depending on materials and compositions of various types of solar cell elements. Moreover, any rational values that can produce the effects of the present invention are encompassed within a technical range of the present invention even if such values are out of the above numerical ranges.

By thus performing evaluation under actual operating conditions, photoelectric conversion performance and/or reliability of a solar cell can be more accurately evaluated. Note, however, that conditions under which the method of the present invention for evaluating a solar cell is carried out are not limited to such actual operating conditions, and vary depending on performance and exposure time of a camera and a defect quantity. Optimum conditions can be appropriately set by a person skilled in the art. For example, optimum conditions can be set in consideration of industrial application conditions (balance between a light emission intensity and a measuring time (cost)) at the present technical level. More specifically, it is only necessary that an amount of an electric current to be applied be increased in a case where it is difficult to detect defects (case where the number of defects is small, case where defects are minute, etc.).

Note that the method of the present invention for evaluating a solar cell is described on the assumption that a solar cell module is constituted by a large number of solar cell elements connected in series. However, even if a solar cell module is constituted by a large number of solar cell elements connected in parallel, the solar cell module can be evaluated for each portion in which solar cell elements are connected in series.

As described above, the method of the present invention for evaluating the solar cell makes it possible to easily and accurately detect a defect of a solar cell and determine whether the defect is an internal cause defect or an external cause defect without requiring a large-sized facility unlike the conventional method for evaluating the solar cell. More specifically, the method according to the present invention for evaluating the solar cell utilize the electroluminescence based on an electric current passage in a forward direction. Thus, the method according to the present invention are advantageous over the conventional art, for example, in (i) it is possible to easily and accurately evaluate type and quantity of defects of a solar cell, (ii) a large facility is not necessary, thus it is possible to evaluate the solar cell as a product (as a product completed in the manufacturing factory or as a product implemented on a construction), (iii) an internal cause defect caused by a physical property of the solar cell can be identified, and it is therefore possible to evaluate impurities contained in a substrate of the solar cell or associated physical properties, (iv) not only a defect of a thin film solar cell using silicon crystal, but also a defect of a solar cell using a different material can be evaluated, and (v) it is not necessary to use a scanning probe (electron beam, laser), thus the measurement can be done easily.

According to the method of the present invention for evaluating a solar cell, in a case where a solar cell module to be evaluated is a solar cell module constituted by a plurality of solar cell elements connected in series, defects in the whole of the solar cell module can be evaluated by passing an electric current once therethrough. That is, by passing the electric current through the solar cell module once, the electric current passes through all the solar cell elements constituting the solar cell module, thereby causing all the solar cell elements to emit light. In this case, the present invention may be arranged to instantaneously and collectively measure an in-plane distribution of light. More specifically, for example, a two-dimensional in-plane distribution of light can be collectively measured by using a CCD or the like as described above, or an in-plane distribution of light can be collectively measured by using a one-dimensional line scanner. Note that the present invention is not limited to these. By detecting light of the whole solar cell module at one time by using large-sized light detecting means or a line scanner that is capable of performing one-dimensional scanning, it is possible to plainly find out which solar cell element of the solar cell module contains a defect. Further, it is possible to determine whether the defect is an internal cause defect or an external cause defect. Further, in a case where the solar cell module is collectively measured, it is possible to observe and analyze the solar cell module successively from the whole solar cell module to a part of a solar cell element by using a zooming operation of a camera or the like.

As described above, a defect of a solar cell module can be very easily evaluated by using the method of the present invention for evaluating a solar cell. It is of course possible to evaluate a defect of only a single solar cell element. A solar cell element or a solar cell module to be evaluated is not limited in size in particular, and can have various sizes.

The method of the present invention for evaluating a solar cell is applicable to a production process of a solar cell module. This makes it possible to detect, in a production process of a solar cell module, an internal cause defect and an external cause defect by always monitoring a light emission intensity of light in the first range emitted from the solar cell module and a light emission intensity of light in the second range emitted from the solar cell module. Consequently, only a portion in which a defect is present can be remedied or replaced with another one.

In a case where a method for producing a solar cell includes, as its step, the above method for evaluating a solar cell, it is possible to automatically perform total inspection. As a result, it is possible to provide a solar cell module which has no defect.

[2. Device for Evaluating Solar Cell]

A device of the present invention for evaluating a solar cell is a device for evaluating a defect of the solar cell which includes an electric current passing section (electric current passing means) for passing, in a forward direction, an electric current through a solar cell element constituting the solar cell; a light emission detecting section (light emission detecting means) for detecting, out of light emitted from the solar cell element by the electric current applied by the electric current passing means, light in a first range of wavelengths from 800 nm to 1300 nm and light in a second range of wavelengths from 1400 nm to 1800 nm; and a judging section (judging means) for distinguishing between an internal cause defect and an external cause defect by using, as indicators, a light emission intensity of the light in the first range and a light emission intensity of the light in the second range out of the light detected by the light emission detecting means. The device is not particularly limited in terms of other specific arrangement, size, shape, etc.

The following describes each section (each means) of the device in detail. Note that the device of the present invention for evaluating a solar cell is for executing the method of the present invention for evaluating a solar cell. Accordingly, as for explanation of the members, the explanation of the steps of the evaluation method is used, and overlapping descriptions are omitted below.

[2-1. Electric Current Passing Section]

The electric current passing section is not limited in particular in terms of its specific arrangement etc., provided that it can pass, in a forward direction, an electric current through a solar cell element constituting a solar cell. That is, the electric current passing section is a section for executing the "electric current passing step" described in [1-1]. The electric current passing section can be, for example, a conventionally known constant current source, constant voltage source, or the like. In a case where a direct current is passed through the solar cell element, the electric current passing section can be a conventionally known direct current power supply. Note that the following describes a case where a direct current is passed through a solar cell element.

It is preferable that the electric current passing section passes an electric current having a substantially same density as an operating electric current of a solar cell element. In particular, in order to generate light in the first range which has a larger light emission intensity and light in the second range which has a larger light emission intensity, the electric current passing section may pass an electric current having a density in the range described in [1-5].

[2-2. Light Emission Detecting Section]

The light emission detecting section is not limited in particular in terms of its specific arrangement etc., provided that it can detect, out of light generated as a result of the passage of the electric current by the electric current passing section, light in a first range of wavelengths from 800 nm to 1300 nm and light in a second range of wavelengths from 1400 nm to 1800 nm. That is, the light emission detecting section is a section for executing the "light emission detecting step" described in [1-2]. As the light emission detecting section, for example, a conventionally known light detecting device such as an InGaAs CCD camera or an image intensifier as described above can be suitably used.

It is preferable that the light emission detecting means includes detecting means that is capable of concurrently detecting the light in the first range and the light in the second range, a band-pass filter which selectively transmits the light in the first range, and a band-pass filter which selectively transmits the light in the second range.

In this case, each of the band-pass filters can be disposed in any position between the solar cell and the light emission detecting section so that light emitted from the solar cell element passes through the band-pass filter before reaching the light emission detecting section. For example, each of the band-pass filters may be provided in a lens part of the light detecting section.

It is especially preferable that each of the band-pass filters is movably disposed between the solar cell and the light emission detecting section so that the light in the first range and the light in the second range can be separately detected. The term "movably" used herein means that the band-pass filters can be moved from or moved onto a path through which the light emitted from the solar cell element reaches the light emission detecting section, and encompasses, for example, "detachably".

This makes it possible to (i) detect light in one range first by allowing transmission of only the light in the one range with the use of one band-pass filter, (ii) then move the one band-pass filter from the path, (iii) subsequently move the other band-pass filter onto the path, and then (iv) detect light in the other range by allowing transmission of only the light in the other range with the use of the other band-pass filter.

[2-3. Judging Section]

The judging section is not limited in particular in terms of its specific arrangement etc., provided that it can distinguish between an internal cause defect and an external cause defect by using, as indicators, a light emission intensity of the light in the first range and a light emission intensity of the light in the second range out of the light detected by the light emission detecting means. That is, the judging section is a section for executing the "judging step" described in [1-3]. For example, a conventionally known arithmetic unit such as a computer can be suitably used as the judging section.

The judging section may make a judgment with the use of images or with the use of only numerical values, as described in the "judging step" explained in [1-3].

The judging section may be arranged to (i) judge that a defect is present, in a case where the light emission intensity of the light in the first range is not more than a first threshold value and (ii) judge that there is an internal cause defect in a portion judged, in the step (i), as a portion having the defect, in a case where the light emission intensity of the light in the second range is not less than a second threshold value in the portion and judge that there is an external cause defect in the portion, in a case where the light emission intensity of the light in the second range is smaller than the second threshold value in the portion.

Further, the judging section may be arranged to (iii) judge, as a portion having an internal cause defect, a portion in which the light emission intensity of the light in the first range is not more than a first threshold value and the light emission intensity of the light in the second range is not less than a second threshold value and (iv) judge, as a portion having an external cause defect, a portion in which the light emission intensity of the light in the first range is not more than the first threshold value and the light emission intensity of the light in the second range is smaller than the second threshold value.

Note that "first threshold value", "second threshold value", and "light emission intensity" have the same meaning as those described in [1-3], and are not explained repeatedly.

[2-4. Image Generating Section]

The device of the present invention for evaluating a solar cell may further include an image generating section. The image generating section is not limited in particular in terms of its specific arrangement etc., provided that it can generate (i) a first image based on the light emission intensity of the light in the first range detected by the light emission detecting section and (ii) a second image based on the light emission intensity of the light in the second range detected by the light emission detecting section. That is, the image generating section is a section for executing the "image generating step" described in [1-4]. For example, a conventionally known light detecting device such as a CCD camera or an image intensifier can be suitably used as the image generating section.

In a case where the device of the present invention for evaluating a solar cell includes the image generating section, the judging section is not limited in particular in terms of its specific arrangement etc., provided that it can distinguish between an internal cause defect and an external cause defect by using, as indicators, (i) the light emission intensity of the light in the first range in the first image generated by the image generating section and (ii) the light emission intensity of the light in the second range in the second image generated by the image generating section. As for the other matters concerning the judging section, the explanation in [2-3] can be referred to, and therefore explanation of the other matters is omitted.

[2-5. Evaluation Apparatus Under Actual Operating Conditions]

As in the above method, an object to be evaluated by the device of the present invention for evaluating a solar cell is not limited in particular, and can be generally a solar cell made of a semiconductor, preferably a solar cell which includes, as its main constituent member, a silicon semiconductor. From such a solar cell element using a silicon semiconductor, light in a first range of wavelengths from 800 nm to 1300 nm, preferably from 900 nm to 1200 nm, more preferably from 1000 nm to 1100 nm is emitted, and light in a second range of wavelengths from 1400 nm to 1800 nm, preferably from 1500 nm to 1700 nm, more preferably from 1550 nm to 1650 nm is emitted. Accordingly, it is preferable that the light emission detecting section is capable of detecting light of wavelengths in these ranges.

Further, the device of the present invention for evaluating a solar cell may include a scanning section (scanning means) that is capable of performing two-dimensional scanning, or a one-dimensional scanning mechanism such as a line scanner. In a case where the device of the present invention for evaluating a solar cell includes the scanning section, a whole large-sized solar cell module including a large number of solar cell elements can be evaluated while being scanned. The scanning section may be provided in the device for evaluating a solar cell or may be provided in a solar cell element to be evaluated. Meanwhile, it is possible to perform the evaluation without scanning. For example, by observation from above the solar cell element, the whole solar cell module may be evaluated at one time or may be evaluated only partially.

Needless to say, regarding matters other than the matters described above, the description regarding the method of the present invention for evaluating a solar cell in [1] can be appropriately referred to and be applied to the device for evaluating a solar cell.

[2-6. Embodiment of Device for Evaluating Solar Cell]

The following describes an embodiment of the device of the present invention for evaluating a solar cell with reference to FIG. 2. As shown in FIG. 2, an evaluation device 10 of the present embodiment for evaluating a solar cell includes a black box 1, a comb-shaped probe 4, a copper plate 5, a direct current power supply 6, an light emission detecting section 12, and a judging section 13. A target to be evaluated by the evaluation device 10 is a solar cell module 7. The solar cell module 7 is constituted by a plurality of solar cell elements that are linked with each other. The solar cell module 7 may be a solar cell panel obtained by combining solar cell modules.

The black box 1 creates a dark state to make detection of light emitted from the solar cell module 7 easier. The black box 1 is provided with a window hole that is used in evaluating a solar cell module or panel that is set up in a perpendicular direction.

The light emission detecting section 12 serves as light emission detecting means including a CCD camera. The light emission detecting section 12 includes an InGaAs CCD camera 2 and a lens 3. The light emission detecting section 12 is 90° rotatable. This makes it possible to evaluate the solar cell module that is set up in the perpendicular direction.

The lens 3 may be a normal lens or zoom lens. On the lens 3, a band-pass filter 14 which selectively transmits light in a first range and a band-pass filter 15 which selectively transmits light in a second range are detachably provided.

In a case in which cells (solar cell elements) constituting the solar cell modules 7 of different sizes are evaluated by using, as the light emission detecting section 12, an InGaAs CCD camera, it is possible to use an InGaAs CCD camera having the following capabilities shown in Table 1.

TABLE 1

CCD Camera
~For Picturing cells in different sizes~
Effective Element Size: 12.29 mm$^2$ Normal Picturing Mode Lens
Capable of picturing the whole by picturing cell by cell.
Picturing Ranges: approx. 15 mm$^2$, 25 mm$^2$, 110 mm$^2$, 160 mm$^2$, 210 mm$^2$
Zooming
Capable of zooming each cell
Minimum Picturing Range: 0.1 mm$^2$
Maximum Picturing Range: 210 mm$^2$
Movable in X and Y axes
Capable of moving in X and Y-axis directions while zooming
Maximum Movable Ranges: approx. 210 mm$^2$
Module Picturing Mode 90° Rotation
Capable of Picturing Module (1200 mm × 800 mm)
Distance between Module and Lens: approx. 3 m
Pictures Module placed out of Black Box.

More specifically, in the normal picturing mode, the picturing is carried out in a state in which a CCD camera is positioned above a solar cell as illustrated in FIG. 2. Meanwhile, in the module picturing mode, a solar cell module is placed outside the black box 1, and the CCD camera is rotated 90° to picture and measure the solar cell module.

The sizes (cell sizes) of the solar cell module 7 to be evaluated in the normal picturing mode may be, for example, approximately 10 mm×10 mm, 20 mm×20 mm, 100 mm×100 mm, 150 mm×150 mm, 160 mm×160 mm, or 200 mm×200 mm in dimension, and 0.3 mm or less in thickness.

In the present embodiment, it is preferable that a distance between the lens 3 of the light emission detecting section 12 and the solar cell module 7 be set to not less than 150 mm and not more than 400 mm, and that the light emission detecting section 12 be movable up and down between the light emission detecting section 12 and the solar cell module 7.

The comb-shaped probe 4 is a surface contact for applying an electric current to the solar cell module 7. The comb-shaped probe 4 includes a pair of comb-shaped probes, as illustrated in FIG. 2. One tooth of the comb-shaped probe 4 corresponds to one electrode of the solar cell element constituting the solar cell module 7. The probe with a comb-shaped structure can apply an electric current evenly on the solar cell module 7, and thus is preferable.

Especially, comb-shaped probes for 100 mm×100 mm, 150 mm×150 mm, and 200 mm×200 mm cells may be arranged to be different in a length and an electrode-electrode width of each pass bar electrode. For example, a pair of comb-shaped probes produced by Atto System Corp can be used. In this case, it is preferable that a distance between the two comb-shaped probes be adjustable. A distance between "tooth" of the comb-shaped probes is not limited in particular, and can be, for example, 9 mm. Moreover, the teeth of the comb-shaped probes may be 1 mm in diameter. It is preferable to use one comb-shaped probe per one electrode.

In a case where the solar cell module 7 has a size of 10 mm×10 mm or 20 mm×20 mm, a probe from a positioner may be used instead of using the comb-shaped probe.

The copper plate 5 functions as a reverse contact. For example, the copper plate 5 may be a gold-plated copper plate. In this case, it is preferable to suck the solar cell element 7 overall. To cope with a consequent change in the cell size, square drains centered at the same center may be provided so as to perform the suction more stably. The drains may have, for example, a size of 8 mm×8 mm, 18 mm×18 mm, 98 mm×98 mm, 148 mm×148 mm, and 195 mm×195 mm. Further, it is preferable to provide a temperature sensor and/or a cooling device. This allows a temperature of the solar cell to be kept constant and allows an improvement in accuracy of measurement and evaluation.

The direct current power supply 6 may be a normal DC power supply (which is capable of passing an electric current having a density of 1 mA/cm$^2$ to 5000 mA/cm$^2$ through a solar cell element). A voltage may be approximately 5V in a case where a solar cell element or a solar cell module is evaluated. However, a voltage of approximately 100V is preferable in a case where a solar cell panel obtained by combining solar cell modules is evaluated. In particular, it is preferable that a voltage is approximately 1 to 2 V for each solar cell element.

The comb-shaped probe 4, the copper plate 5, and the direct current power supply 6 serve as an electric current passing section 11. The comb-shaped probe 4 is fixedly connected to a negative side of the direct current power supply 6 and the copper plate 5 is fixedly connected to a positive side of the direct current power supply 6.

The judging section 13 serves as judging means for evaluating a defect of the solar cell module 7. In the present embodiment, an image processor is used as the judging section 13. Software to be used is not limited in particular, provided that the object of the present invention can be achieved. For example, software configured as follows is preferably used.

Capable of storing a 8-bit image ($2^8$=256 gray scales) or 16-bit image ($2^{16}$=65536 gray scales).
Capable of acquiring and storing luminance profile data of an area selected on a screen after detecting (picturing) light emitted from the solar cell element.
Capable of dealing with spectrum.
Capable of acquiring highly-sensitive image (image intensifier camera), e.g., capable of measuring emission at a reverse current application.

It is more preferable that the software has the following configuration.

improved in that an image obtained from data read by a spreadsheet software is rotated 90° to the pictured image.

Capable of easily switching to a beginning mode.

Programmed to automatically create a histogram of the light emission intensity.

Automatically measures a length and weight of a portion having low light emission intensity (i.e. a dark portion). Automatically measures dark portions of 1 cm or greater in size.

Calculates an average of the intensities of the light emission in a selected range (preferably being capable of measuring an average of the intensities with grid portions omitted).

Inside the black box 1, the light emission detecting section 12, the comb-shaped probe 4, the copper plate 5, and the solar cell module 7 are disposed. The light emission detecting section 12 is positioned to be able to detect the light emission intensities of the solar cell module 7. In the present embodiment, the light emission detecting section 12 is disposed above the solar cell module 7.

An embodiment of an evaluation operation of the evaluation device 10 is described with reference to FIG. 3. First, the electric current passing section 11 passes an electric current through the solar cell module 7. The solar cell module 7 emits light due to the electric current thus passed through the solar cell module 7. This light passes through the band-pass filter 14, which selectively transmits light in a first range, and then enters the light emission detecting section 12. The light emission detecting section 12 thus detects the light in the first range emitted from the solar cell module 7. Next, the band-pass filter 14, which selectively transmits the light in the first range, is detached, and the band-pass filter 15, which selectively transmits light in a second range, is attached. The light from the solar cell module 7 passes through the band-pass filter 15, which selectively transmits the light in the second range, and then enters the light emission detecting section 12. The light emission detecting section 12 thus detects the light in the second range emitted from the solar cell module 7.

The light emission detecting section 12 and the judging section 13 are connected to each other. The light emission detecting section 12 detects the light in the first range and the light in the second range, and supplies a result of the detection to the judging section 13. On the basis of the result of the detection, the judging section 13 compares a light emission intensity of the light in the first range with a first threshold value and compares a light emission intensity of the light in the second range with a second threshold value. Thus, the judging section 13 judges a type of a defect in the solar cell module 7.

In this case, a result of the detection of the light in the first range and a result of the detection of the light in the second range may be separately supplied to the judging section 13 or simultaneously supplied to the judging section 13. In a case where the result of the detection of the light in the first range and the result of the detection of the light in the second range are separately supplied to the judging section 13, the light emission intensity of the light in the first range can be compared with the first threshold value first, and then the light emission intensity of the light in the second range can be compared with the second threshold value or vice versa. Meanwhile, in a case where the result of the detection of the light in the first range and the result of the detection of the light in the second range are simultaneously supplied to the judging section 13, the light emission intensity of the light in the first range and the light emission intensity of the light in the second range can be concurrently compared with the first threshold value and the second threshold value, respectively.

Another embodiment of the device of the present invention for evaluating a solar cell is described below. An evaluation device 110 of the present embodiment for evaluating a solar cell is identical to the evaluation device 10 except for that the evaluation device 110 further includes an image generating section 16.

Figure 4:
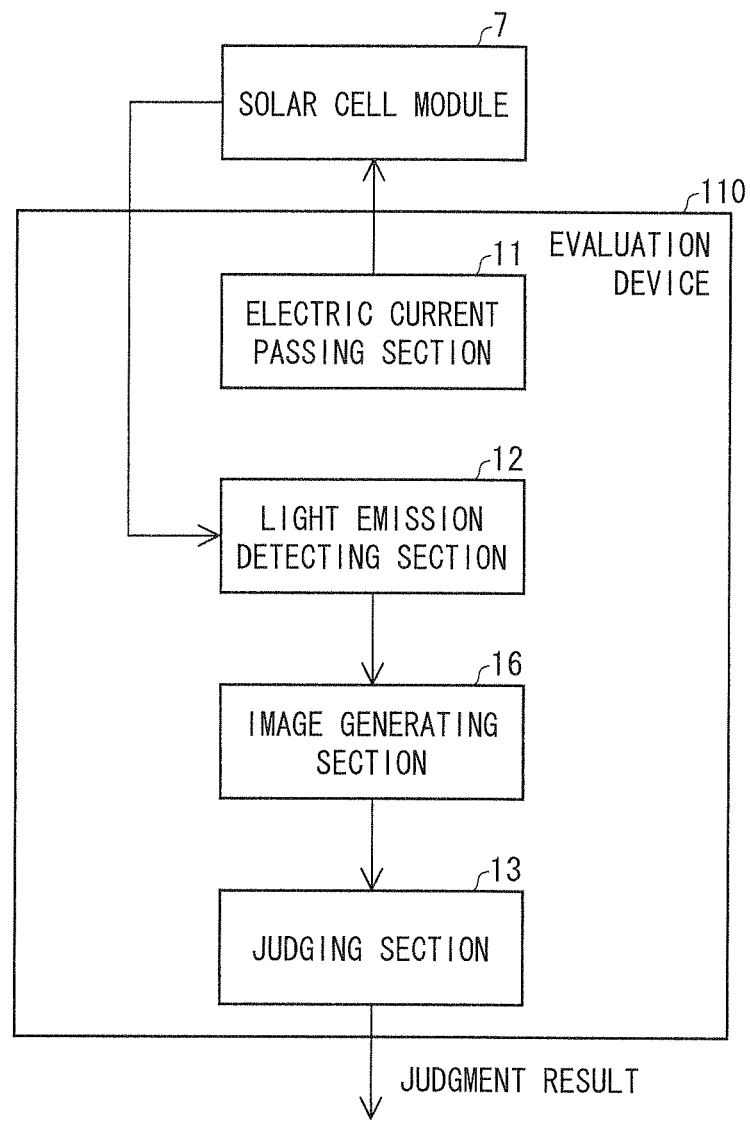
FIG. 4 is a functional block diagram schematically illustrating another example of the device of the present embodiment for evaluating a solar cell.

Another embodiment of an evaluation operation of the evaluation device 110 for evaluating a solar cell is described with reference to FIG. 4. First, the electric current passing section 11 passes an electric current to the solar cell module 7. The solar cell module 7 emits light due to the electric current thus passed through the solar cell module 7. This light passes through the band-pass filter 14, which selectively transmits light in a first range, and then enters the light emission detecting section 12. The light emission detecting section 12 thus detects the light in the first range emitted from the solar cell module 7. Next, the band-pass filter 14, which selectively transmits the light in the first range, is detached, and the band-pass filter 15, which selectively transmits light in a second range, is attached. The light from the solar cell module 7 passes through the band-pass filter 15, which selectively transmits the light in the second range, and then enters the light emission detecting section 12. The light emission detecting section 12 thus detects the light in the second range emitted from the solar cell module 7.

Next, the light emission detecting section 12 supplies a signal of the light in the first range and a signal of the light in the second range to the image generating section 16. The image generating section 16 generates, based on these signals, an image (first image) indicative of a light emission intensity of the light in the first range and an image (second image) indicative of a light emission intensity of the light in the second range, and supplies data of the first image and the second image to the judging section 13. In a case where the light emission detecting section 12 includes, as a light detecting section, a CCD camera or an image intensifier for example, such a light detecting section can not only detect the light in the first range and the light in the second range, but also generate images on the basis of signals of the light thus detected and supply data of the images to the judging section 13. That is, such a light detecting section also serves as the image generating section 16. In the present embodiment, the InGaAs CCD camera 2 serves as the image generating section 16.

The judging section 13 compares, on the basis of the data of the first image and the second image, the light emission intensity of the light in the first range and the light emission intensity of the light in the second range with the first threshold value and the second threshold value, respectively. Thus, the judging section 13 judges a type of a defect in the solar cell module 7.

In this case, a result of the detection of the light in the first range (the data of the first image) and a result of the detection of the light in the second range (the data of the second image) may be separately supplied to the judging section 13 or simultaneously supplied to the judging section 13. In a case where the result of the detection of the light in the first range and the result of the detection of the light in the second range are separately supplied to the judging section 13, the light emission intensity of the light in the first range can be compared with the first threshold value first, and then the light emission intensity of the light in the second range can be compared with the second threshold value or vice versa. Meanwhile, in a case where the result of the detection of the light in the first range and the result of the detection of the light in the second range are simultaneously supplied to the judging section 13, the light emission intensity of the light in the first range and the light emission intensity of the light in the second range can be concurrently compared with the first threshold value and the second threshold value, respectively.

As described above, according to the device of the present invention for evaluating a solar cell, the method for evaluating a solar cell can be easily and surely carried out. In this case, a large-sized and complicated device like the conventional evaluating device is not required, and a defect can be detected and evaluated accurately with a simple arrangement.

It should be noted that the present invention is not limited to the above description in which the device and method for evaluating the solar cell element and the solar cell module are explained. The present invention is also applicable to evaluation of a solar cell panel formed by linking a plurality of the solar cell modules. In this case, a density of an electric current to be applied, a voltage, a shape of the probe, etc. can be changed according to need. For example, it may be arranged such that the forward current is equivalent to a total current of currents in a range of 1 to 5000 [$mA/cm^2$] per solar cell element. Moreover, a dark room may be used in replacement of the black box according to the size of the solar cell module. Moreover, as described above, the light emission detecting section 12 in FIG. 2 may be rotated 90° to picture a solar cell module that is set up in a perpendicular direction.

In actual use of the device of the present invention for evaluating a solar cell, a user must carry out the operation in a dark room in order that light of specific wavelengths out of light emitted from a solar cell element due to electroluminescence can be efficiently selectively detected by the light emission detecting section. Accordingly, operation efficiency is poor. Measures against such a problem include, for example, improvement in sensitivity of the light detecting section such as a CCD camera, development of a band-pass filter which transmits light of specific wavelengths efficiently, improvement of an environment for blocking surrounding disturbing light (use of lighting which emits only light of specific wavelengths), etc. By taking such measures, a user can avoid an operation in a dark room, and therefore can carry out the operation efficiently.

[3. Usage]

As described above, the method and device of the present invention for evaluating a solar cell do not need a large-sized facility and can evaluate a defect of the solar cell easily, as compared with conventional method and device for evaluating a solar cell.

Furthermore, it is possible to establish a business model such as a maintenance method and a maintenance system for regularly evaluating a solar cell implemented on a construction because, unlike the conventional arts, (i) the method and device of the present invention for evaluating the solar cell do not need a scanning probe (electron beam, laser) and thus are able to perform easier measurement and (ii) the method and device of the present invention for evaluating the solar cell do not need a large-sized facility, and it is therefore possible to observe and evaluate the solar cell as a product (as a product completed in the manufacturing factory or as a product implemented on a construction).

That is, the present invention encompasses a method for performing maintenance of a solar cell, the method including the above-described evaluation device evaluating a defect of a solar cell implemented on a construction, and a replacement instructing device instructing, based on a result of the evaluation by the evaluation device, a solar-cell-element-replacing party to replace a solar cell element having an internal cause defect and/or an external cause defect.

Furthermore, the present invention encompasses a maintenance system for performing the maintenance method. The maintenance system according to the present invention at least includes the evaluation device as described above, and a replacement instructing device for instructing, based on a result of the evaluation by the evaluation device, a solar-cell-element-replacing party to replace a solar cell element having an internal cause defect and/or an external cause defect out of solar cell elements of a solar cell implemented on a construction.

Means by which the replacement instructing device instructs a solar-cell-element-replacing party to replace a solar cell element is not limited in particular, and the replacement instructing device can instructs, via a communication network, a solar-cell-element-replacing party to replace a solar cell element.

In the present Description, what is meant by the wording "solar cell module implemented on a construction" is a solar cell module that is already implemented on a construction such as residential facilities such as living houses, condominiums etc., business facilities such as shopping malls, office buildings, etc., or the like. Extruded from the "solar cell module implemented on a construction" is a solar cell that is being produced or is just produced in the manufacturing factory of the solar cell module, and that is not implemented on any construction, for example.

Figure 5:
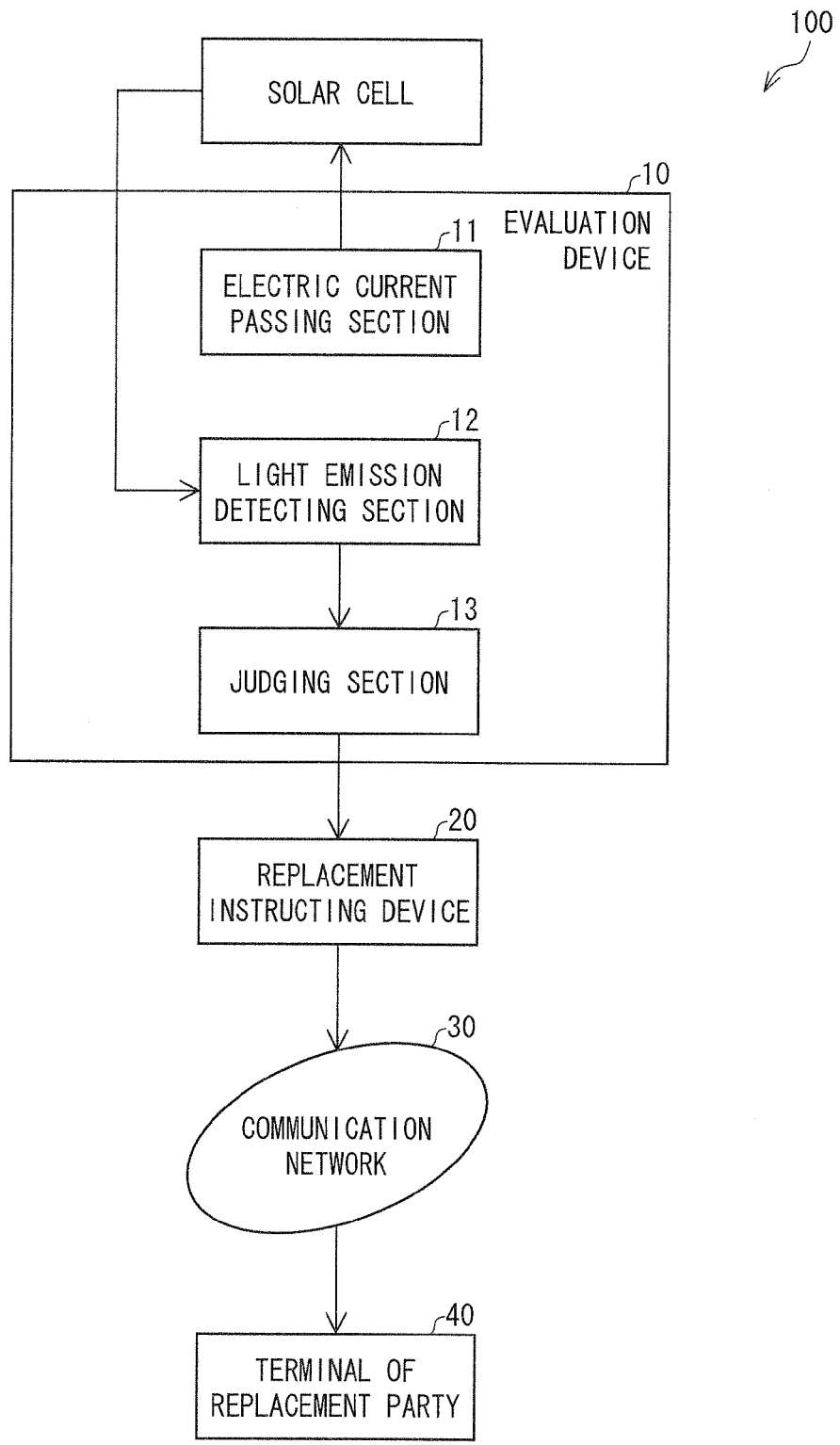
FIG. 5 is a functional block diagram schematically illustrating an example of a maintenance system of the present embodiment.

FIG. 5 illustrates a functional block diagram schematically illustrating one example of the maintenance system according to the present embodiment. As illustrated in FIG. 5, a maintenance system 100 according to the present invention includes an evaluation device 10 and a replacement instructing device 20. The evaluation device 10 includes an electric current passing section 11, a light emission detecting section 12, and a judging section 13. Instead of the evaluation device 10, an evaluation device 110 (not shown) may be used which includes an electric current passing section 11, a light emission detecting section 12, an image generating section 16, and a judging section 13.

The replacement instructing device 20 is connected to a terminal 40 of a replacement party via a communication network 30. The communication network 30 and/or the terminal 40 of the replacement party may be included in the maintenance system or may be a given external network or a given terminal.

The electric current passing section 11, the light emission detecting section 12, the image generating section 16, and the judging section 13 carry out the electric current passing step, the light emission detecting step, the image generating step, and the judging step, respectively.

The replacement instructing device 20 instructs, via a communication network, the replacement party for the solar cell element to replace a solar cell element whose performance is lower than a predetermined value. The replacement instructing device 20 can be, for example, an arithmetic device, such as a computer, which is connectable to a communication line such as Internet.

Needless to say, one computer may function as the judging section and the replacement instructing device, while the present embodiment is arranged such that the judging section 13 and the replacement instructing device 20 are individual devices.

Moreover, the communication network 30 may be a wired leased line or a communication line such as the Internet or the like. Moreover, the communication network 30 may be a network using a portable phone line or a wireless line.

The terminal 40 of the replacement party may be any terminal, provided that it can recognize the replacement instruction from the replacement instructing device 20. It is preferable that the terminal 40 be provided with a display section (e.g., a display such as CRT or LCD) or an output section (e.g., a printer).

Figure 6:
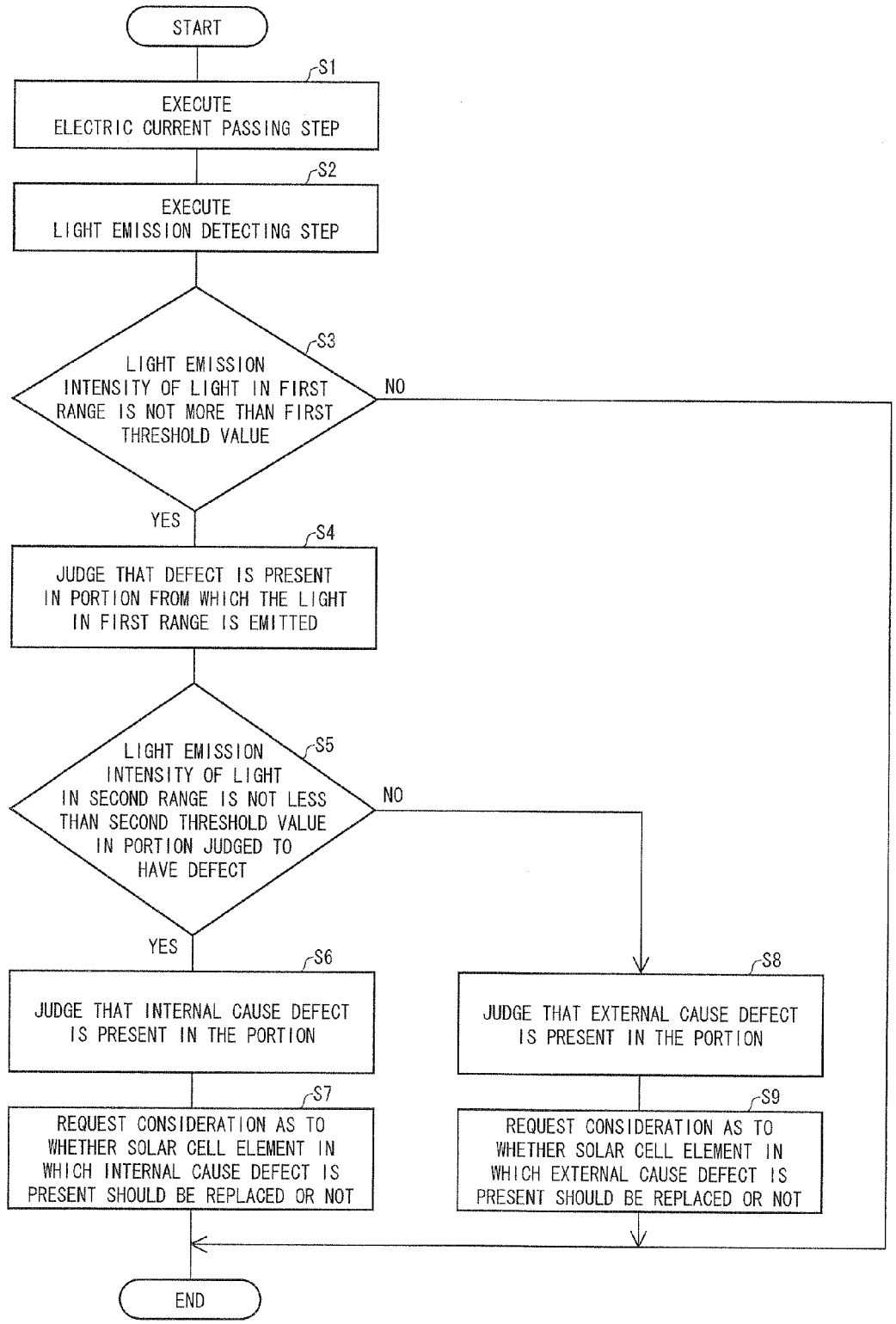
FIG. 6 is a diagram illustrating an example of a flow of the maintenance system of the present embodiment.

FIG. 6 illustrates one example of a flow of the maintenance system of the embodiment using the evaluation device 10. In this flow, first, a portion of a solar cell in which portion a defect is present is specified on the basis of a light emission intensity of light in a first range, and then it is determined, on the basis of a light emission intensity of light in a second range in the portion thus specified, whether the defect is an internal cause defect or an external cause defect.

As illustrated in FIG. 6, in the maintenance system 100, the electric current passing section 11 of the evaluation device 10 performs the electric current passing step with respect to a solar cell module that is a target of the maintenance (Step 1, the step will be abbreviated as "S" hereinafter). Next, the light emission detecting section 12 of the evaluation device 10 detects light in the first range and the light in the second range which are emitted from the solar cell module due to the process in S1 (S2).

Next, the judging section 13 judges, on the basis of a result of the detection by the light emission detecting section 12, whether or not a light emission intensity of the light in the first range is not more than a first threshold value (S3). In a case where the judging section 13 judges, in S3, that the light emission intensity of the light in the first range is not more than the first threshold value ("Y"), the process in S4 is carried out. In S4, the judging section 13 judges that a defect is present in a portion from which the light in the first range is emitted. Then, the process in S5 is carried out. In S5, the judging section 13 judges whether or not a light emission intensity of the light in the second range is not less than a second threshold value in the portion judged to have the defect. In a case where the judging section 13 judges, in S5, that the light emission intensity of the light in the second range is not less than the second threshold value ("Y"), the process in S6 is carried out. In S6, the judging section 13 judges that an internal cause defect is present in the portion, and supplies this result to the replacement instructing device 20. Then, the process in S7 is carried out. In S7, the replacement instructing device 20 notifies, via the communication network 30, the terminal 40 of the replacement party of presence of a solar cell element in which the internal cause defect is present, and requests the replacement party to consider whether the solar cell element should be replaced or not. Thus, the process is terminated.

Meanwhile, in a case where the judging section 13 judges, in S5, that the light emission intensity of the light in the second range is smaller than the second threshold value ("N"), the process in S8 is carried out. In S8, the judging section 13 judges that an external cause defect is present in the portion, and supplies this result to the replacement instructing device 20. Then, the process in S9 is carried out. In S9, the replacement instructing device 20 notifies, via the communication network 30, the terminal 40 of the replacement party of presence of a solar cell element in which the external cause defect is present, and requests the replacement party to consider whether the solar cell element should be replaced or not. Thus, the process is terminated.

In a case where the judging section 13 judges, in S3, that the light emission intensity of the light in the first range is larger than the first threshold value ("N"), the process is terminated.

According to such a flow, first, it is determined whether or not a defect is present in a solar cell, and then a type of the defect is evaluated. This makes it possible to more speedily specify a solar cell in which a defect is present from among solar cells most of which has no defect, and is therefore preferable.

Figure 7:
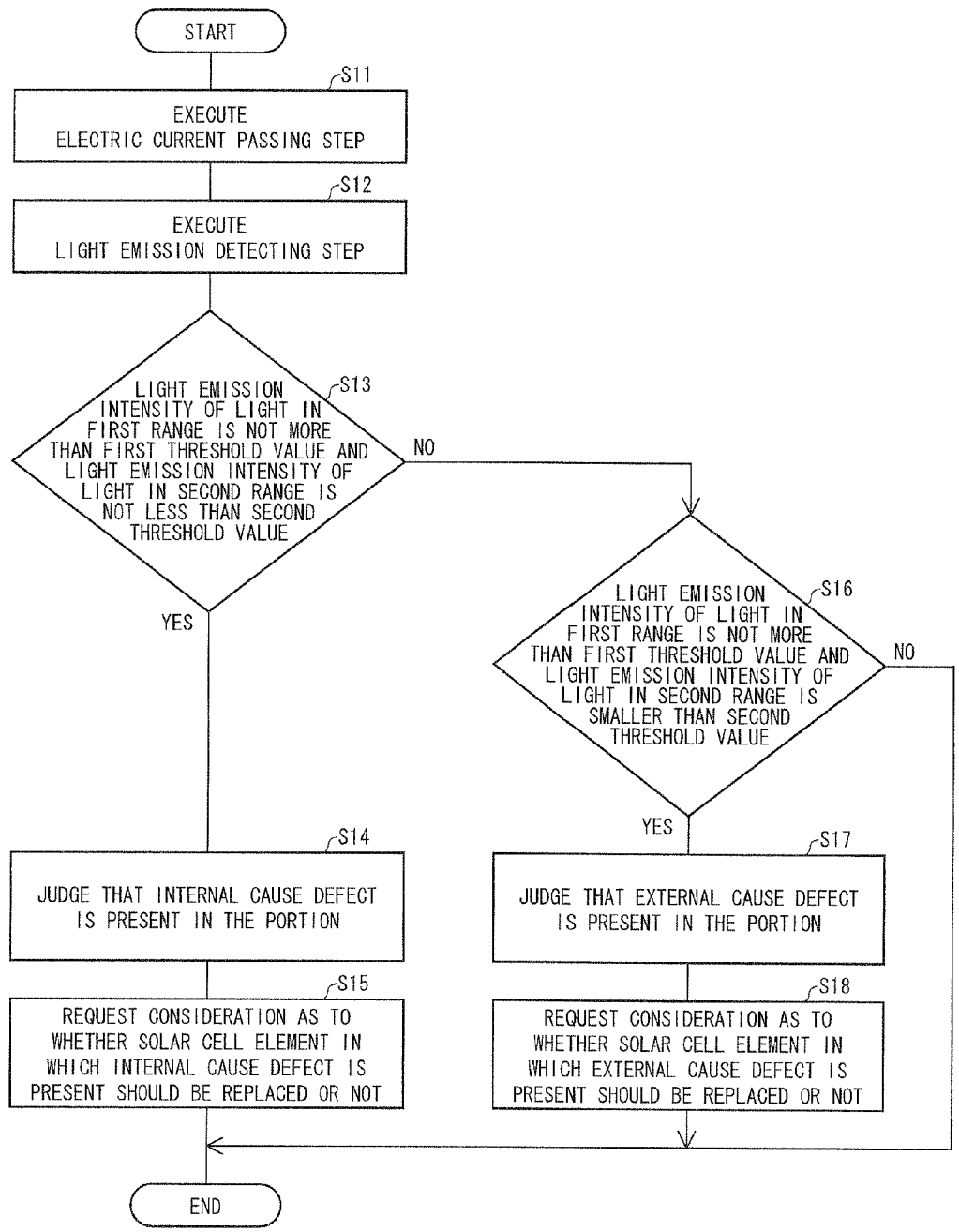
FIG. 7 is a diagram illustrating another example of a flow of the maintenance system of the present embodiment.

Next, FIG. 7 illustrates another example of the flow of the maintenance system of the embodiment using the evaluation device 10. In this flow, the light emission intensity of the light in the first range and the light emission intensity of the light in the second range are concurrently compared with the first threshold value and the second threshold value, respectively, and thus it is determined whether a defect in a solar cell is an internal cause defect or an external cause defect.

As illustrated in FIG. 7, in the maintenance system 100, the electric current passing section 11 of the evaluation device 10 performs the electric current passing step with respect to a solar cell module that is a target of the maintenance (S11). Next, the light emission detecting section 12 of the evaluation device 10 detects light in the first range and the light in the second range which are emitted from the solar cell module due to the process in S11 (S12).

Next, the judging section 13 judges, on the basis of a result of the detection by the light emission detecting section 12, whether or not (i) a light emission intensity of the light in the first range is not more than a first threshold value and (ii) a light emission intensity of the light in the second range is not less than a second threshold value (S13). In a case where the judging section 13 judges, in S13, that (i) the light emission intensity of the light in the first range is not more than the first threshold value and (ii) the light emission intensity of the light in the second range is not less than the second threshold value ("Y"), the process in S14 is carried out. In S14, the judging section 13 judges that an internal cause defect is present in a portion from which the light in the first range and the light in the second range are emitted, and supplies this result to the replacement instructing device 20. Then, the process in S15 is carried out. In S15, the replacement instructing device 20 notifies, via the communication network 30, the terminal 40 of the replacement party of presence of a solar cell element in which the internal cause defect is present, and requests the replacement party to consider whether the solar cell element should be replaced or not. Thus, the process is terminated.

Meanwhile, in a case where the judging section 13 does not judge, in S13, that (i) the light emission intensity of the light in the first range is not more than the first threshold value and (ii) the light emission intensity of the light in the second range is not less than the second threshold value ("N"), the process in S16 is carried out. In S16, the judging section 13 judges, on the basis of the result of the detection by the light emission detecting section 12, whether or not (i) the light emission intensity of the light in the first range is not more than the first threshold value and (ii) the light emission intensity of the second range is smaller than the second threshold value. In a case where the judging section 13 judges, in S16, that (i) the light emission intensity of the light in the first range is not more than the first threshold value and (ii) the light emission intensity of the light in the second range is smaller than the second threshold value ("Y"), the process in S17 is carried out. In S17, the judging section 13 judges that an external cause defect is present in a portion from which the light in the first range and the light in the second range are emitted, and supplies this result to the replacement instructing device 20. Then, the process in S18 is carried out. In S18, the replacement instructing device 20 notifies, via the communication network 30, the terminal 40 of the replacement party of presence of a solar cell element in which the external cause defect is present, and requests the replacement party to consider whether the solar cell element should be replaced or not. Thus, the process is terminated.

In a case where the judging section 13 does not judge, in S16, that (i) the light emission intensity of the light in the first range is not more than the first threshold value and (ii) the light emission intensity of the light in the second range is smaller than the second threshold value ("N"), the process is terminated. Note that the order in which the processes in S13 through S15 and the processes in S16 through S18 are carried out is not limited in particular. The processes in S13 through S15 may be carried out after the processes in S16 through S18 are carried out. Alternatively, the processes in S13 through S15 and the processes in S16 through S18 may be carried out concurrently. Especially such a flow in which the processes in S13 through S15 and the processes in S16 through S18 are carried out concurrently is preferable in a case where more speedy evaluation than that in the flow of S1 through S9 is required.

Figure 8:
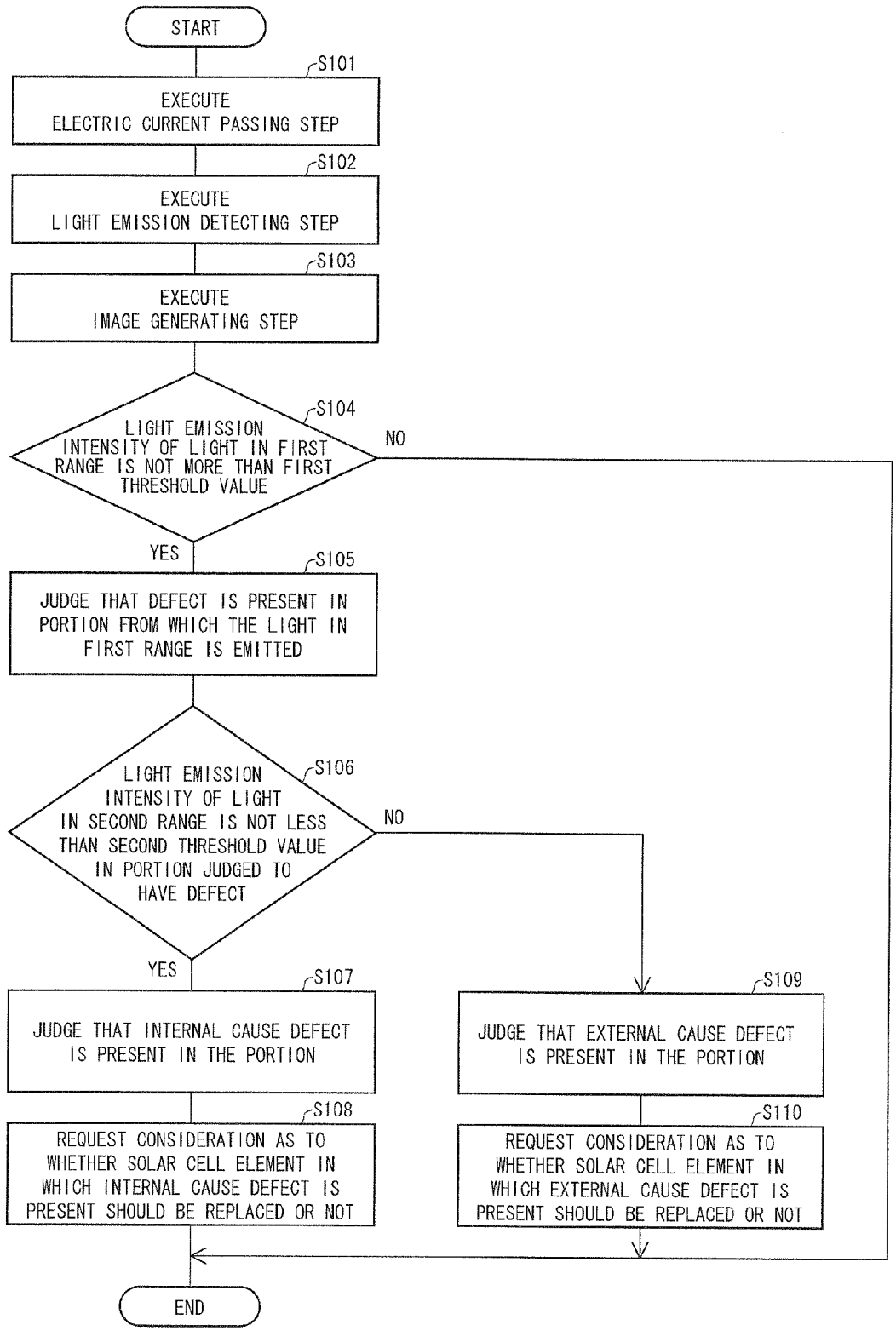
FIG. 8 is a diagram illustrating still another example of a flow of the maintenance system of the present embodiment.

Next, FIG. 8 illustrates one example of a flow of the maintenance system of the embodiment using the evaluation device 110. In this flow, first, a portion of a solar cell in which portion a defect is present is specified on the basis of a light emission intensity of light in a first range, and then it is determined, on the basis of a light emission intensity of light in a second range in the portion thus specified, whether the defect is an internal cause defect or an external cause defect.

As illustrated in FIG. 8, in the maintenance system 100, the electric current passing section 11 of the evaluation device 110 performs the electric current passing step with respect to a solar cell module that is a target of the maintenance (S101). Next, the light emission detecting section 12 of the evaluation device 110 detects light in the first range and the light in the second range which are emitted from the solar cell module due to the process in S101 (S102).

Then, the image generating section 16 generates a first image of the light in the first range on the basis of a light emission intensity of the light in the first range detected by the light emission detecting section 12 and generates a second image of the light in the second range on the basis of a light emission intensity of the light in the second range detected by the light emission detecting section 12 (S103).

Next, the judging section 13 judges, based on the first image and the second image generated by the image generating section 16, whether or not the light emission intensity of the light in the first range is not more than a first threshold value (S104). In a case where the judging section 13 judges, in S104, that the light emission intensity of the light in the first range is not more than the first threshold value ("Y"), the process in S105 is carried out. In S105, the judging section 13 judges that a defect is present in a portion from which the light in the first range is emitted. Then, the process in S106 is carried out. In S106, the judging section 13 judges whether or not the light emission intensity of the light in the second range emitted from the portion judged to have a defect is not less than a second threshold value. In a case where the judging section 13 judges, in S106, that the light emission intensity of the light in the second range is not less than the second threshold value ("Y"), the process in S107 is carried out. In S107, the judging section 13 judges that an internal cause defect is present in the portion, and supplies this result to the replacement instructing device 20. Then, the process in S108 is carried out. In S108, the replacement instructing device 20 notifies, via the communication network 30, the terminal 40 of the replacement party of presence of a solar cell element in which the internal cause defect is present, and requests the replacement party to consider whether the solar cell element should be replaced or not. Thus, the process is terminated.

Meanwhile, in a case where the judging section 13 judges, in S106, that the light emission intensity of the light in the second range is smaller than the second threshold value ("N"), the process in S109 is carried out. In S109, the judging section 13 judges that an external cause defect is present in the portion, and supplies this result to the replacement instructing device 20. Then, the process in S110 is carried out. In S110, the replacement instructing device 20 notifies, via the communication network 30, the terminal 40 of the replacement party of presence of a solar cell element in which the external cause defect is present, and requests the replacement party to consider whether the solar cell element should be replaced or not. Thus, the process is terminated.

In a case where the judging section 13 judges, in S104, that the light emission intensity of the light in the first range is larger than the first threshold value ("N"), the process is terminated.

According to such a flow, first, it is determined whether or not a defect is present in a solar cell, and then a type of the defect is evaluated. This makes it possible to more speedily specify a solar cell in which a defect is present from among solar cells most of which has no defect, and is therefore preferable.

Figure 9:
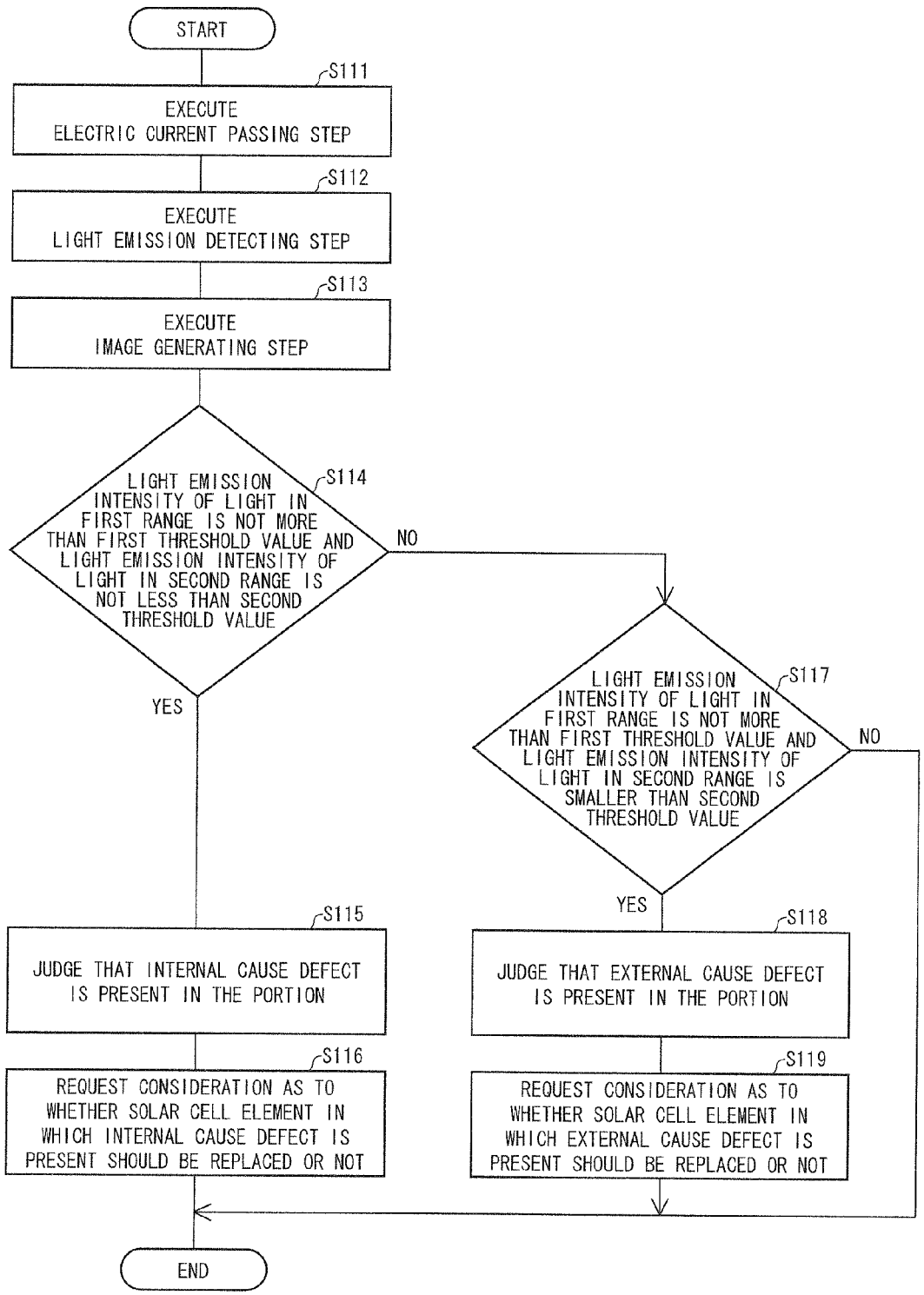
FIG. 9 is a diagram illustrating still another example of a flow of the maintenance system of the present embodiment.

Next, FIG. 9 illustrates another example of the flow of the maintenance system of the present embodiment using the evaluation device 110. In this flow, the light emission intensity of the light in the first range and the light emission intensity of the light in the second range are concurrently compared with the first threshold value and the second threshold value, respectively, and thus it is determined whether a defect in a solar cell is an internal cause defect or an external cause defect.

As illustrated in FIG. 9, in the maintenance system 100, the electric current passing section 11 of the evaluation device 110 performs the electric current passing step with respect to a solar cell module that is a target of the maintenance (S111). Next, the light emission detecting section 12 of the evaluation device 110 detects light in the first range and the light in the second range which are emitted from the solar cell module due to the process in S111 (S112).

Then, the image generating section 16 generates a first image of the light in the first range on the basis of a light emission intensity of the light in the first range detected by the light emission detecting section 12 and generates a second image of the light in the second range on the basis of a light emission intensity of the light in the second range detected by the light emission detecting section 12 (S113).

Next, the judging section 13 judges, based on the first image and the second image generated by the image generating section 16, whether or not (i) the light emission intensity of the light in the first range is not more than a first threshold value and (ii) the light emission intensity of the light in the second range is not less than a second threshold value (S114). In a case where the judging section 13 judges, in S114, that (i) the light emission intensity of the light in the first range is not more than the first threshold value and (ii) the light emission intensity of the light in the second range is not less than a second threshold value ("Y"), the process in S115 is carried out. In S115, the judging section 13 judges that an internal cause defect is present in a portion from which the light in the first range and the light in the second range are emitted, and supplies this result to the replacement instructing device 20. Then, the process in S116 is carried out. In S116, the replacement instructing device 20 notifies, via the communication network 30, the terminal 40 of the replacement party of presence of a solar cell element in which the internal cause defect is present, and requests the replacement party to consider whether the solar cell element should be replaced or not. Thus, the process is terminated.

Meanwhile, in a case where the judging section 13 does not judge, in S114, that (i) the light emission intensity of the light in the first range is not more than the first threshold value and (ii) the light emission intensity of the light in the second range is not less than the second threshold value ("N"), the process in S117 is carried out. In S117, the judging section 13 judges, based on the first image and the second image generated by the image generating section 16, whether or not (i) the light emission intensity of the light in the first range is not more than the first threshold value and (ii) the light emission intensity of the light in the second range is smaller than the second threshold value. In a case where the judging section 13 judges, in S117, that (i) the light emission intensity of the light in the first range is not more than the first threshold value and (ii) the light emission intensity of the light in the second range is smaller than the second threshold value ("Y"), the process in S118 is carried out. In S118, the judging section 13 judges that an external cause defect is present in a portion from which the light in the first range and the light in the second range are emitted, and supplies this result to the replacement instructing device 20. Then, the process in S119 is carried out. In S119, the replacement instructing device 20 notifies, via the communication network 30, the terminal 40 of the replacement party of presence of a solar cell element in which the external cause defect is present, and requests the replacement party to consider whether the solar cell element should be replaced or not. Thus, the process is terminated.

In a case where the judging section 13 does not judge, in S117, that (i) the light emission intensity of the light in the first range is not more than the first threshold value and (ii) the light emission intensity of the light in the second range is smaller than the second threshold value ("N"), the process is terminated. Note that the order in which the processes in S114 through S116 and the processes in S117 through S119 are carried out is not limited in particular. The processes in S114 through S116 may be carried out after the processes in S117 through S119 are carried out. Alternatively, the processes in S114 through S116 and the processes in S117 through S119 may be carried out concurrently. Especially such a flow in which the processes in S114 through S116 and the processes in S117 through S119 are carried out concurrently is preferable in a case where more speedy evaluation than that in the flow of S101 through S110 is required.

Conventionally, solar cell evaluation requires a large-sized device. Accordingly, it has been difficult to evaluate a solar cell implemented on a construction such as houses etc. and to regularly perform maintenance of such an implemented solar cell. By contrast, the solar cell maintenance method and maintenance system of present invention do not require a large-sized device, and make it possible to evaluate quality of a solar cell easily with the use of a simple evaluation device. It is therefore possible to regularly perform maintenance of even a solar cell implemented on a construction (i.e., solar cell that has been produced). Consequently, quality of a solar cell module can be kept at a certain level.

Moreover, the solar cell maintenance method and maintenance system of the present invention make it possible to judge at one sight, by using a light emission characteristic as an indicator, which solar cell element is poor in performance and/or reliability among many solar cell elements constituting the solar cell module. Thus, it is not necessary to replace the whole solar cell module, and only the solar cell element whose performance is poor can be replaced. That is, efficiency is very high. Therefore, the present invention is applicable not only to product inspection in the production of the solar cell module but also to the maintenance thereof, thereby contributing to popularizing the solar cell module. As such, the present invention is not only industrially applicable but also very useful for the earth environment.

Moreover, for example, the use of the solar cell maintenance method and maintenance system of the present invention also make it possible to perform maintenance without external light (for example at night or in a dark room), by picturing light emission from the solar cell element with a CCD camera and comparing the pictured image with predetermined reference data in color thickness (i.e., performing comparison process by computer-using data processing or the like). In this case, for example, it is possible to judge that it is time to replace a solar cell element when portions where a light emission intensity of light in the first range declines and a light emission intensity of light in the second range increases or declines are present at a certain percentage or more.

It should be noted that, needless to say, various evaluating devices described in the present Description are suitably applicable to the maintenance method and maintenance system, albeit the above explanation discusses the maintenance method and maintenance system using some examples of the evaluation device for the solar cell.

Finally, blocks of the maintenance system such as the evaluation device, replacement instructing device etc. (hereinafter these blocks are referred to merely as "evaluation device etc.") may be realized by way of hardware or software as executed by a CPU as follows:

The evaluation device etc. each include a CPU (central processing unit) and memory devices (memory media). The CPU (central processing unit) executes instructions in control programs realizing the functions. The memory devices include a ROM (read only memory) which contains programs, a RAM (random access memory) to which the programs are loaded, and a memory containing the programs and various data. The objective of the present invention can also be achieved by mounting to the evaluation device etc. a computer-readable storage medium containing control program code (executable program, intermediate code program, or source program) for the evaluation device etc., which is software realizing the aforementioned functions, in order for the computer (or CPU, MPU) to retrieve and execute the program code contained in the storage medium.

The storage medium may be, for example, a tape, such as a magnetic tape or a cassette tape; a magnetic disk, such as a Floppy (Registered Trademark) disk or a hard disk, or an optical disk, such as CD-ROM/MO/MD/DVD/CD-R; a card, such as an IC card (memory card) or an optical card; or a semiconductor memory, such as a mask ROM/EPROM/EEPROM/flash ROM.

Figure 10:
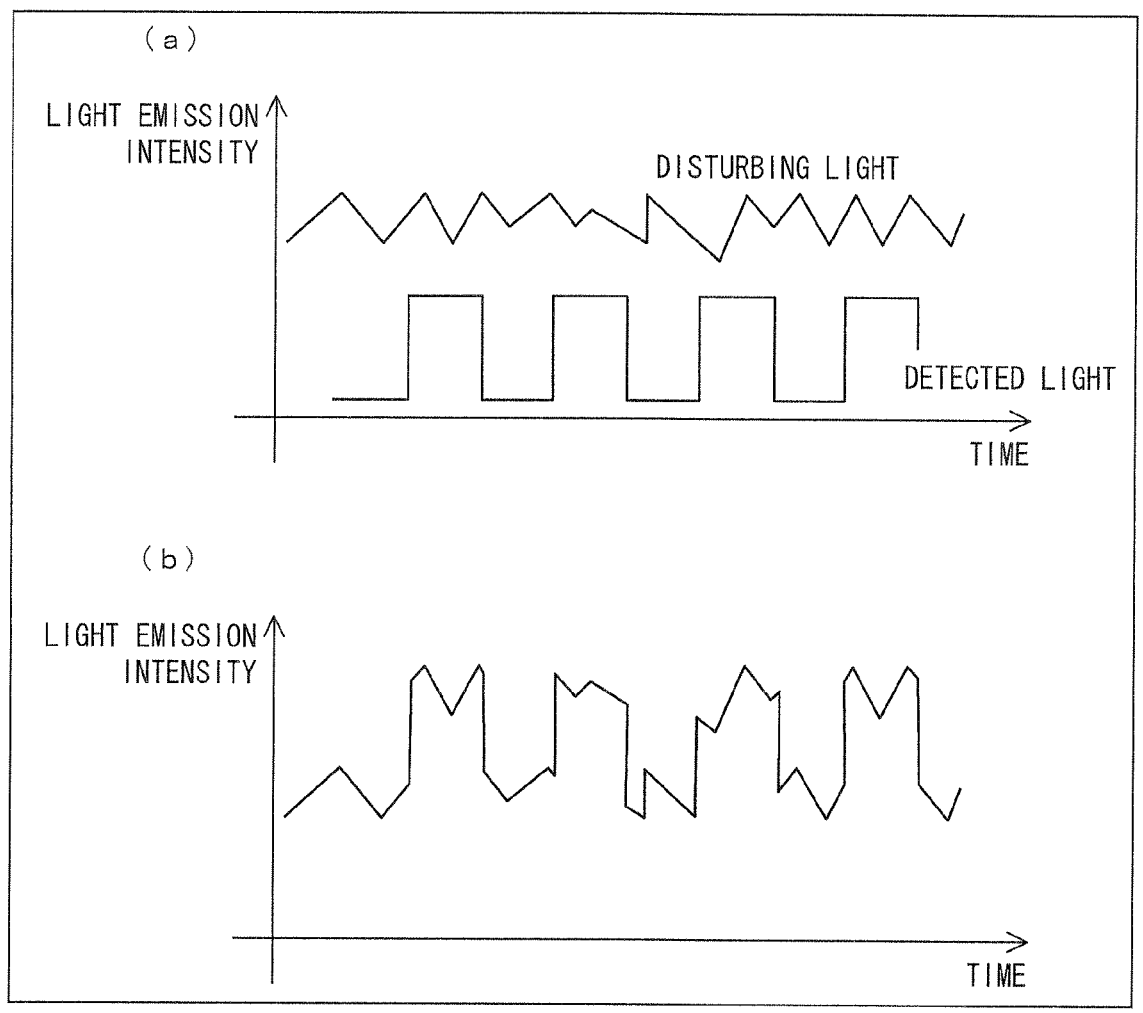
FIG. 10 is a diagram explaining a method for reducing noise caused by disturbing light detected in the light emission detecting step in a case where a pulse current is used.

The evaluation device etc. may be arranged to be connectable to a communications network so that the program code may be delivered over the communications network. The communications network is not limited in any particular manner, and may be, for example, the Internet, an intranet, extranet, LAN, ISDN, VAN, CATV communications network, virtual dedicated network (virtual private network), telephone line network, mobile communications network, or satellite communications network. The transfer medium which makes up the communications network is not limited in any particular manner, and may be, for example, wired line, such as IEEE 1394, USB, electric power line, cable TV line, telephone line, or ADSL line; or wireless, such as infrared radiation (IrDA, remote control), Bluetooth (Registered Trademark), 802.11 wireless, HDR, mobile telephone network, satellite line, or terrestrial digital network. The present inven- The above description dealt with method and device for evaluating a solar cell by passing a direct current through a solar cell element, and use thereof. The following describes method and device for evaluating a solar cell by passing a pulse current through a solar cell element, and use thereof. Use of a pulse current makes it possible to reduce, by a known method, noise caused by disturbing light detected in the light emission detecting step. The known method is a method in which the disturbing light and detected light (i.e., light in the first range or light in the second range) are detected in synchronization as illustrated in (a) of FIG. 10, and intensities of the disturbing light and detected light are added together so that noise caused by the disturbing light is cancelled as illustrated in (b) of FIG. 10.

In the method for evaluating a solar cell by passing a pulse current, a pulse current is passed through a solar cell element with the use of a conventionally known pulse power supply in the electric current passing step. By passing the pulse current through the solar cell element, transient light emission is observed. In the light emission detecting step, light in the first range and light in the second range in this transient light emission are detected.

In the image generating step, a trap density (first trap density) of an electric charge in the solar cell element is calculated on the basis of a light emission intensity of the light in the first range in the transient light emission. A method for calculating such a trap density is known to a person skilled in the art. Similarly, a trap density (second trap density) of an electric charge in the solar cell element is calculated on the basis of a light emission intensity of the light in the second range in the transient light emission. Then, a first image based on the first trap density and a second image based on the second trap density are generated. In a case where a pulse current is used, what is meant by "image based on light emission intensity" generated in the image generating step is an image indicative of a trap density of an electric charge in a solar cell element.

In the judging step, an internal cause defect and an external cause defect are distinguished from each other by using, as indicators, the first trap density in the first image and the second trap density in the second image. Specifically, in the judging step, for example, (v) it is determined that a defect is present, in a case where the first trap density is not more than a third threshold value, and (vi) in a case where the second trap density is not less than a fourth threshold value in a portion judged, in the step (v), as a portion having a defect, it is determined that an internal cause defect is present in the portion, whereas in a case where the second trap density is smaller than the fourth threshold value in a portion judged, in the step (v), as a portion having a defect, it is determined that an external cause defect is present in the portion.

It is also possible that (vii) a portion in which the first trap density is not more than the third threshold value and the second trap density is not less than the fourth threshold value is judged as a portion having an internal cause defect, and (viii) a portion in which the first trap density is not more than the third threshold value and the second trap density is smaller than the fourth threshold value is judged as a portion having an external cause defect. The order in which the step (vii) and the step (viii) are carried out is not limited in particular. The step (viii) may be carried out after the step (vii) or vice versa. Alternatively, the step (vii) and the step (viii) may be carried out concurrently.

The "third threshold values" in the steps (v) through (viii) may be different from each other or identical to each other, and the "fourth threshold values" in the step (v) through (viii) may be different from each other or identical to each other. For example, there may be a case where the "third threshold value" used in the step (v) is identical to the "third threshold value" used in the steps (vii) and (viii), and the "fourth threshold value" used in the step (vi) is identical to the "fourth threshold value" used in the steps (vii) and (viii).

Further, the "threshold values" may be set, for example, by (i) specifying, in advance by use of a conventionally known method, portions of the solar cell element in which portions an internal cause defect and/or an external cause defect is present, and (ii) turning, into numerical values, the first trap density and the second trap density in these portions. For example, the "third threshold value" may be a value of a first trap density based on a light emission intensity of transient light of a first range emitted from a normal portion of a solar cell element by passing a pulse current through the solar cell element in the electric current passing step or may be 90%, 80%, 70%, 60%, 50%, 40%, 30%, 20%, or 10% of the first trap density.

Similarly, the "fourth threshold value" may be a value of a second trap density based on a light emission intensity of transient light in a second range emitted from an internal cause defect portion of a solar cell element by passing a pulse current through the solar cell element in the electric current passing step or may be a value slightly smaller than the second trap density, for example, approximately 90%, 80%, 70%, 60%, or 50% of the second trap density.

As for the matters other than the matters described above, the explanation in [1] can be appropriately referred to.

A method for producing a solar cell module includes, as one step, such a method for evaluating a solar cell. Further, a device for evaluating a solar cell carries out such a method for evaluating a solar cell. As for the other matters, the explanation in [2] can be appropriately referred to. Similarly, a maintenance method of a solar cell uses the device for evaluating a solar cell, and a maintenance system of a solar cell carries out the maintenance method of a solar cell. As for the other matters, the explanation in [3] can be appropriately referred to.

As described above, it is possible to distinguish between an internal cause defect and an external cause defect that are present in a solar cell element by carrying out spectroscopic analysis of light emission caused by electroluminescence through a specific electronic level. This spectroscopic analysis is applicable not only to distinguishment between the internal cause defect and the external cause defect, but also to assessment of a segregation state of specific impurities because it is possible to know a two-dimensional in-plane distribution of physical properties due to light emission caused by electroluminescence. Further, this spectroscopic analysis makes it possible to analyze functions of each element in a so-call tandem-type solar cell module having a composite structure in which solar cell elements are provided in plural layers.

The present invention encompasses the following embodiments.

The device of the present invention for evaluating a solar cell is preferably arranged to further include image generating means for generating (i) a first image based on the light emission intensity of the light in the first range detected by the light emission detecting means and (ii) a second image based on the light emission intensity of the light in the second range detected by the light emission detecting means, the judging means distinguishing between the internal cause defect and the external cause defect by using, as indicators, the light emission intensity of the light in the first range in the first image generated by the image generating means and the light emission intensity of the light in the second range in the second image generated by the image generating means.

The device of the present invention for evaluating a solar cell is preferably arranged such that the electric current passed by the electric current passing means is a direct current.

The device of the present invention for evaluating a solar cell is preferably arranged such that an amount of the electric current passed by the electric current passing means is equivalent to a density of a photocurrent generated by light irradiation of the solar cell element.

The device of the present invention for evaluating a solar cell is preferably arranged such that $j1<j2$ and/or $t1<t2$ are satisfied where j1 is an amount of the electric current passed through the solar cell element by the electric current passing means in order to detect the light in the first range, t1 is a period of time taken for the light emission detecting means to detect the light in the first range, j2 is an amount of the electric current passed through the solar cell element by the electric current passing means in order to detect the light in the second range, and t2 is a period of time taken for the light emission detecting means to detect the light in the second range.

The device of the present invention for evaluating a solar cell is preferably arranged such that the light emission detecting means detects the light with use of (i) light detecting means that is capable of simultaneously detecting the light in the first range and the light in the second range, (ii) a band-pass filter which selectively transmits the light in the first range, and (iii) a band-pass filter which selectively transmits the light in the second range.

The device of the present invention for evaluating a solar cell is preferably arranged such that the light detecting means includes a CCD camera or an image intensifier.

The device of the present invention for evaluating a solar cell is preferably arranged such that the judging means (i) judges that a defect is present, in a case where the light emission intensity of the light in the first range is not more than a first threshold value, and (ii) judges that an internal cause defect is present in a portion judged to have the defect, in a case where the light emission intensity of the light in the second range is not less than a second threshold value in the portion, and judges that an external cause defect is present in the portion, in a case where the light emission intensity of the light in the second range is smaller than the second threshold value in the portion.

The device of the present invention for evaluating a solar cell is preferably arranged such that the judging means (iii) judges that an internal cause defect is present in a portion in which the light emission intensity of the light in the first range is not more than a first threshold value and the light emission intensity of the light in the second range is not less than a second threshold value, and (iv) judges that an external cause defect is present in a portion in which the light emission intensity of the light in the first range is not more than the first threshold value and the light emission intensity of the light in the second range is smaller than the second threshold value.

The device of the present invention for evaluating a solar cell is preferably arranged such that the solar cell element includes, as a main constituent member, a silicon semiconductor.

The method of the present invention for evaluating a solar cell is preferably arranged to further include the step of (d) generating (i) a first image based on the light emission intensity of the light in the first range detected in the step (b) and (ii) a second image based on the light emission intensity of the light in the second range detected in the step (b), in the step (c), the internal cause defect and the external cause defect are distinguished from each other by using, as indicators, light emission intensity of the light in the first range in the first image generated in the step (d) and the light emission intensity of the light in the second range in the second image generated in the step (d).

The method of the present invention for evaluating a solar cell is preferably arranged such that the electric current passed in the step (a) is a direct current.

The method of the present invention for evaluating a solar cell is preferably arranged such that an amount of the electric current passed in the step (a) is equivalent to a density of a photocurrent generated by light irradiation of the solar cell element.

The method of the present invention for evaluating a solar cell is preferably arranged such that $j1<j2$ and/or $t1<t2$ are satisfied where j1 is an amount of the electric current passed through the solar cell element in the step (a) in order to detect the light in the first range, t1 is a period of time for the detection of the light in the first range in the step (b), j2 is an amount of the electric current passed through the solar cell element in the step (a) in order to detect the light in the second range, and t2 is a period of time for detection of the light in the second range in the step (b).

The method of the present invention for evaluating a solar cell is preferably arranged such that in the step (b), the light is detected with use of (i) light detecting means that is capable of simultaneously detecting the light in the first range and the light in the second range, (ii) a band-pass filter which selectively transmits the light in the first range, and (iii) a band-pass filter which selectively transmits the light in the second range.

The method of the present invention for evaluating a solar cell is preferably arranged such that the light detecting means includes a CCD camera or an image intensifier.

The method of the present invention for evaluating a solar cell is preferably arranged such that the step (c) includes the steps of: (i) judging that a defect is present, in a case where the light emission intensity of the light in the first range is not more than a first threshold value, and (ii) judging that an internal cause defect is present in a portion judged, in the step (i), to have the defect, in a case where the light emission intensity of the light in the second range is not less than a second threshold value in the portion, and judging that an external cause defect is present in the portion, in a case where the light emission intensity of the light in the second range is smaller than the second threshold value in the portion.

The method of the present invention for evaluating a solar cell is preferably arranged such that the step (c) includes the steps of: (iii) judging that an internal cause defect is present in a portion in which the light emission intensity of the light in the first range is not more than a first threshold value and the light emission intensity of the light in the second range is not less than a second threshold value, and (iv) judging that an external cause defect is present in a portion in which the light emission intensity of the light in the first range is not more than the first threshold value and the light emission intensity of the light in the second range is smaller than the second threshold value.

The method of the present invention for evaluating a solar cell is preferably arranged such that the solar cell element includes, as a main constituent member, a silicon semiconductor.

A method of the present invention for maintenance of a solar cell includes the steps of: the device of the present invention evaluating a defect of a solar cell implemented on a construction; and a replacement instructing device instructing, based on a result of the evaluation by the device, a replacement party to replace a solar cell element in which the internal cause defect and/or the external cause defect is present.

A system of the present invention for maintenance of a solar cell includes: the device of the present invention for evaluating a solar cell; and a replacement instructing device which instructs, based on a result of evaluation by the device, a replacement party to replace a solar cell element in which the internal cause defect and/or the external cause defect is present out of solar cell elements of a solar cell implemented on a construction.

A method present invention for producing a solar cell module includes, as one step, the method of the present invention for evaluating a solar cell.

The embodiments of the present invention are described in more details referring to Example below. Needless to say, the present invention is not limited to the following Example and can be altered in details in various ways. Further, the present invention is not limited to the description of the embodiments above, but may be altered by a skilled person within the scope of the claims. An embodiment based on a proper combination of technical means disclosed in different embodiments is encompassed in the technical scope of the present invention.

Example

An electric current was passed, in a forward direction, through a solar cell module including a plurality of solar cell elements made from a polycrystalline silicon semiconductor, and light generated due to the passage of the electric current was analyzed. In the present Example, an InGaAs CCD camera (Xenics, XEVA-1.7 series) was used to picture this light.

First, light emission intensity (luminescence intensity) and spectral characteristics of light generated by passing an electric current of 40 mA/cm$^2$ through the solar cell module was analyzed. The result is shown in (a) of FIG. 11. Note that the spectral characteristics were measured with the use of a spectrometer (JASCO Corp. M50) according to its operation manual. The broken line in (a) of FIG. 11 indicates a wavelength range (wavelengths in a range from 200 nm to 1200 nm) of light detected with the use of a Si CCD camera, and the dashed-dotted line in (a) of FIG. 11 indicates a wavelength range (wavelengths in a range from 800 nm to 1800 nm) of light detected with the use of an InGaAs CCD camera.

As illustrated in (a) of FIG. 11, in a case where the electric current is passed through the solar cell module, light having a strong light emission intensity in wavelengths from 800 nm to 1300 nm was observed from the silicon semiconductor constituting the solar cell element.

Next, light emission intensity and spectral characteristics of light emitted when the electric current was passed through the solar cell module were analyzed with the use of an InGaAs CCD camera provided with a band-pass filter (band-pass filter for wavelength of 1100 nm: BROAD BANDPASS FILTER (BBP-0910-1170C produced by SPECTROGON) which selectively transmits light of a wavelength range indicated by the black arrow in (a) of FIG. 11. As a result, in a case where the InGaAs CCD camera is provided with the band-pass filter for the wavelength of 1100 nm, light having a strong light emission intensity in wavelengths from 845 nm to 1205 nm could be detected.

Further, it is reported that, in a case where the electric current was passed through the solar cell module, light having a strong light emission intensity in wavelengths from 1400 nm to 1800 nm was observed from the silicon semiconductor constituting the solar cell element, as shown in (a) of FIG. 11. In a case where the InGaAs CCD camera is provided with a band-pass filter (band-pass filter for a wavelength of 1500 nm: for example, BROAD BANDPASS FILTER (BBP-1350-1600C produced by SPECTROGON) which selectively transmits light of a wavelength range indicated by the gray arrow, light having a strong light emission intensity in wavelengths from 1320 nm to 1640 nm can be detected.

(b) of FIG. 11 shows characteristics of the band-pass filter for the wavelength of 1100 nm, and (c) of FIG. 11 shows characteristics of the band-pass filter for the wavelength of 1500 nm.

Next, as shown in (a) and (b) of FIG. 12, a solar cell module (ISC (short-circuit current)=700 mA) in which solar cell elements each having a size of 4 cm×3 cm are disposed in a lattice pattern was used as a sample. An electric current was passed through this solar cell module, and light emission from the solar cell module was pictured with the use of an InGaAs CCD camera provided with a band-pass filter for a wavelength of 1100 nm or a band-pass filter for wavelength 1500 nm.

First, an electric current of 400 mA was passed through the solar cell module for 20 milliseconds, and light emission from the solar cell module was pictured with the use of the InGaAs CCD camera via the band-pass filter for a wavelength of 1100 nm for 3 seconds in total. The result is shown in (a) of FIG. 12. Next, an electric current of 1000 mA was passed through the solar cell module for 80 milliseconds, and light emission from the solar cell module was pictured with the use of the InGaAs CCD camera via the band-pass filter for a wavelength of 1500 nm for 20 seconds in total. The result is shown in (b) of FIG. 12. Note that (a) and (b) of FIG. 12 show the same portion of the solar cell module.

As shown in (a) and (b) of FIG. 12, in a case where the electric current was passed through the solar cell module and light of the wavelength of 1100 nm or light of the wavelength of 1500 nm emitted from the solar cell elements were observed, it was revealed that there are portions whose color ranges from white to black in the solar cell elements. In (a) and (b) of FIG. 12, the light emission becomes stronger as the color becomes closer to white, whereas the light emission becomes weaker as the color becomes closer to black. A portion between adjacent solar cell elements does not emit light, and is therefore black.

Next, relationship between the light emission and defects of the solar cell was analyzed in detail by enlarging (a) and (b) of FIG. 12. (c), (e), and (g) of FIG. 12 are enlarged views of A, B, and C shown in (a) of FIG. 12, respectively. (d), (f), and (h) of FIG. 12 are enlarged views of A', B', and C' shown in (b) of FIG. 12, respectively.

As a result, it was revealed that the light emission of the wavelength of 1100 nm was caused by interband transition of the solar cell, whereas the light in the vicinity of the wavelength of 1500 nm was caused by an internal cause defect of the solar cell element. Further, it was revealed that light emission in the entire wavelength range declines in a portion where an external cause defect is present.

Accordingly, it was revealed that white portions (light-emitting portions) indicated by the white arrows in (c), (e), and (g) of FIG. 12 were normal portions having no internal cause defect and no external cause defect and that portions (non-light-emitting portions) indicated by the black arrows and the white triangles in (c), (e), and (g) of FIG. 12 are portions in which an internal cause defect or an external cause defect is present.

Next, by comparing (c) and (d) of FIG. 12, and (e) and (f) of FIG. 12, and (g) and (h) of FIG. 12, portions which do not emit light in (c), (e), and (g) of FIG. 12 but emit light in (d), (f), and (h) of FIG. 12 could be identified as portions (portions indicated by the white triangles in (c) through (h) of FIG. 12) in which an internal cause defect is present. Further, portions which do not emit light both in (c), (e), and (g) of FIG. 12 and do not emit light also in (d), (f), and (h) of FIG. 12 (portions indicated by the black arrows in (c) through (h) of FIG. 12) could be identified as portions in which an external cause defect is present.

INDUSTRIAL APPLICABILITY

A method etc. of the present invention for evaluating a defect of a solar cell is applicable not only to defect evaluation, quality inspection, and element material evaluation performed at production of a solar cell module, but also to regular maintenance of a solar cell module that has been already implemented. Thus, the industrial applicability of the present invention is very wide, being not limited to inspecting devices etc.

REFERENCE SIGNS LIST

10: Evaluation device
11: Electric current passing section (electric current passing means)
12: Light emission detecting section (light emission detecting means)
13: Judging section (judging device, judging means)
16: Image generating section (image generating means)
20: Replacement instructing device
30: Communication network
100: Maintenance system
110: Evaluation device

The invention claimed is:

1. A device for evaluating a defect of a solar cell, comprising:
   electric current passing means for passing, in a forward direction, an electric current through a solar cell element constituting the solar cell;
   light emission detecting means for detecting, out of light emitted from the solar cell element due to the electric current passed by the electric current passing means, light in a first range of wavelengths from 800 nm to 1300 nm and light in a second range of wavelengths from 1400 nm to 1800 nm; and
   judging means for distinguishing between an internal cause defect and an external cause defect by using, as indicators, a light emission intensity of the light in the first range and a light emission intensity of the light in the second range out of the light detected by the light emission detecting means.

2. The device according to claim 1, further comprising image generating means for generating (i) a first image based on the light emission intensity of the light in the first range detected by the light emission detecting means and (ii) a second image based on the light emission intensity of the light in the second range detected by the light emission detecting means,
   the judging means distinguishing between the internal cause defect and the external cause defect by using, as indicators, the light emission intensity of the light in the first range in the first image generated by the image generating means and the light emission intensity of the light in the second range in the second image generated by the image generating means.

3. The device according to claim 1, wherein the electric current passed by the electric current passing means is a direct current.

4. The device according to claim 1, wherein an amount of the electric current passed by the electric current passing means is equivalent to a density of a photocurrent generated by light irradiation of the solar cell element.

5. The device according to any claim 1, wherein:
   j1<j2 and/or t1<t2 are satisfied
   where j1 is an amount of the electric current passed through the solar cell element by the electric current passing means in order to detect the light in the first range, t1 is a period of time taken for the light emission detecting means to detect the light in the first range, j2 is an amount of the electric current passed through the solar cell element by the electric current passing means in order to detect the light in the second range, and t2 is a period of time taken for the light emission detecting means to detect the light in the second range.

6. The device according to claim 1, wherein the light emission detecting means detects the light with use of (i) light detecting means that is capable of simultaneously detecting the light in the first range and the light in the second range, (ii) a band-pass filter which selectively transmits the light in the first range, and (iii) a band-pass filter which selectively transmits the light in the second range.

7. The device according to claim 6, wherein the light detecting means includes a CCD camera or an image intensifier.

8. The device according to claim 1, wherein the judging means (i) judges that a defect is present, in a case where the light emission intensity of the light in the first range is not more than a first threshold value, and (ii) judges that an internal cause defect is present in a portion judged to have the defect, in a case where the light emission intensity of the light in the second range is not less than a second threshold value in the portion, and judges that an external cause defect is present in the portion, in a case where the light emission intensity of the light in the second range is smaller than the second threshold value in the portion.

9. The device according to claim 1, wherein the judging means (iii) judges that an internal cause defect is present in a portion in which the light emission intensity of the light in the first range is not more than a first threshold value and the light emission intensity of the light in the second range is not less than a second threshold value, and (iv) judges that an external cause defect is present in a portion in which the light emission intensity of the light in the first range is not more than the first threshold value and the light emission intensity of the light in the second range is smaller than the second threshold value.

10. The device according to any claim 1, wherein the solar cell element includes, as a main constituent member, a silicon semiconductor.

11. A method for maintenance of a solar cell comprising the steps of:
    a device as set forth in claim 1 evaluating a defect of a solar cell implemented on a construction; and
    a replacement instructing device instructing, based on a result of the evaluation by the device, a replacement party to replace a solar cell element in which the internal cause defect and/or the external cause defect is present.

12. A system for maintenance of a solar cell comprising:
    a device as set forth in claim 1; and
    a replacement instructing device which instructs, based on a result of evaluation by the device, a replacement party to replace a solar cell element in which the internal cause defect and/or the external cause defect is present out of solar cell elements of a solar cell implemented on a construction.

13. A method for evaluating a defect of a solar cell, comprising the steps of:
(a) passing, in a forward direction, an electric current through a solar cell element constituting the solar cell;
(b) detecting, out of light emitted from the solar cell element due to the electric current passed in the step (a), light in a first range of wavelengths from 800 nm to 1300 nm and light in a second range of wavelengths from 1400 nm to 1800 nm; and
(c) distinguishing between an internal cause defect and an external cause defect by using, as indicators, a light emission intensity of the light in the first range and a light emission intensity of the light in the second range out of the light detected in the step (b).

14. The method according to claim 13, further comprising the step of (d) generating (i) a first image based on the light emission intensity of the light in the first range detected in the step (b) and (ii) a second image based on the light emission intensity of the light in the second range detected in the step (b),
in the step (c), the internal cause defect and the external cause defect are distinguished from each other by using, as indicators, the light emission intensity of the light in the first range in the first image generated in the step (d) and the light emission intensity of the light in the second range in the second image generated in the step (d).

15. The method according to claim 13, wherein the electric current passed in the step (a) is a direct current.

16. The method according to claim 13, wherein an amount of the electric current passed in the step (a) is equivalent to a density of a photocurrent generated by light irradiation of the solar cell element.

17. The device according to claim 13, wherein:
$j1<j2$ and/or $t1<t2$ are satisfied
where $j1$ is an amount of the electric current passed through the solar cell element in the step (a) in order to detect the light in the first range, $t1$ is a period of time for the detection of the light in the first range in the step (b), $j2$ is an amount of the electric current passed through the solar cell element in the step (a) in order to detect the light in the second range, and $t2$ is a period of time for detection of the light in the second range in the step (b).

18. The method according to claim 13, wherein in the step (b), the light is detected with use of (i) light detecting means that is capable of simultaneously detecting the light in the first range and the light in the second range, (ii) a band-pass filter which selectively transmits the light in the first range, and (iii) a band-pass filter which selectively transmits the light in the second range.

19. The method according to claim 13, wherein the step (c) includes the steps of: (i) judging that a defect is present, in a case where the light emission intensity of the light in the first range is not more than a first threshold value, and (ii) judging that an internal cause defect is present in a portion judged, in the step (i), to have the defect, in a case where the light emission intensity of the light in the second range is not less than a second threshold value in the portion, and judging that an external cause defect is present in the portion, in a case where the light emission intensity of the light in the second range is smaller than the second threshold value in the portion.

20. The method according to claim 13, wherein the step (c) includes the steps of: (iii) judging that an internal cause defect is present in a portion in which the light emission intensity of the light in the first range is not more than a first threshold value and the light emission intensity of the light in the second range is not less than a second threshold value, and (iv) judging that an external cause defect is present in a portion in which the light emission intensity of the light in the first range is not more than the first threshold value and the light emission intensity of the light in the second range is smaller than the second threshold value.

21. The method according to claim 13, wherein the solar cell element includes, as a main constituent member, a silicon semiconductor.

22. A method for producing a solar cell module comprising, as one step, a method as set forth in claim 13.

* * * * *